United States Patent
Matta et al.

(10) Patent No.: US 8,278,072 B1
(45) Date of Patent: Oct. 2, 2012

(54) METHOD FOR SYNTHESIS OF SIALYLATED PRODUCTS USING REVERSIBLE SIALYLATION

(75) Inventors: Khushi L. Matta, Williamsville, NY (US); Edaya V. Chandrasekaran, Northbrook, IL (US); Sriram Neelamegham, Getzville, NY (US); Jun Xue, Langhorne, PA (US)

(73) Assignees: Health Research, Inc., Buffalo, NY (US); The Research Foundation of State University of New York, Amherst, NY (US)

( * ) Notice: Subject to any disclaimer, the term of this patent is extended or adjusted under 35 U.S.C. 154(b) by 870 days.

(21) Appl. No.: 12/274,142

(22) Filed: Nov. 19, 2008

Related U.S. Application Data

(60) Provisional application No. 60/989,030, filed on Nov. 19, 2007.

(51) Int. Cl.
*C12P 19/18* (2006.01)

(52) U.S. Cl. .......................................................... 435/97

(58) Field of Classification Search ........................ None
See application file for complete search history.

(56) References Cited

OTHER PUBLICATIONS

Chandrasekaran et al., "Reversible Sialylation: Synthesis of Cytidine 5'-Monophospho-N-acetylneuraminic Acid from Cytidine 5'Monophosphate with R2,3-Sialyl O-Glycan-, Glycolipid-, and Macromolecule-Based Donors Yields Diverse Sialylated Products", Biochemistry, 2008, 47: 320-330.*

Haverkamp et al.; Determination of the .beta.-Anomeric Configuration of Cytidine 5'-Monophospho-N-acetylneuraminic Acid by carbon-13 NMR Spectroscopy; American Chemical Society, 1979, vol. 101; pp. 4851-4853.

Kolter et al.; Sialic acids—why always alpha-linked?; Glycobiology, vol. 7, No. 7, 1997; pp. vii-ix.

* cited by examiner

*Primary Examiner* — Suzanne M Noakes
(74) *Attorney, Agent, or Firm* — Hodgson Russ LLP

(57) ABSTRACT

A method for producing sialylated molecules based on reverse sialylation that catalytically transfers the sialic acid moiety of sialylated donors to nucleotide monophosphates or transfer sialic acid moieties from sialylated donors to acceptor glycoproteins or glycolipids.

12 Claims, 13 Drawing Sheets

Scheme I

METHOD FOR SYNTHESIS OF SIALYLATED PRODUCTS USING REVERSIBLE SIALYLATION

This application claims priority to U.S. Provisional application No. 60/989,030, filed on Nov. 19, 2007, the disclosure of which is incorporated herein by reference.

This work was supported by funding from the National Institutes of Health under grant no. CA35329 and HL63014 and from the Department of Defense under grant no. W81XWH-06-1-0013. The Government has certain rights in the invention.

BACKGROUND OF THE INVENTION

The sialylation of carbohydrates is catalyzed by sialyltransferases (sialylTs) and trans-sialidases. During the biosynthesis of glycoconjugates, enzymes belonging to the glycosyltransferase family (including sialylTs) catalyze the transfer of a monosaccharide unit from an activated glycosyl donor to an appropriate acceptor molecule. In the case of sialic acid (NeuAc), the activated donor is considered to be NeuAc that is β-glycosidically linked to the aglycan cytidine 5'-monophosphate (CMP) to form CMP-NeuAc (1). In contrast to other activated nucleotide sugars, CMP-NeuAc contains a monophosphate. This activated sugar is also unique since it forms α-glycosidically linked sialic acid residues in nature (2).

While CMP-NeuAc is considered to be useful as a sialic acid donor in sialylation reactions, because it is currently prepared by chemical synthesis, its use as a sialic acid donor is not cost efficient. Thus, there is an ongoing, unmet need for a cost effective method for the preparation of CMP-NeuAc.

SUMMARY OF THE INVENTION

The abbreviations used herein are: sialylT=sialyltransferases; TS=trans-sialidases; AA-CP=Acrylamide copolymer; Al=Allyl; Bn=Benzyl; Me=Methyl; BSM=Bovine Submaxillary Mucin; CGM=Porcine Cowper's Gland Mucin; CMP=Cytidine 5'-monophosphate; FOG=Fetuin O-glycosidic Glycopeptide; FTG=Fetuin Triantennary Glycopeptide; Fuc=fucose; Gal=galactose; GalNAc=N-acetylgalactosamine; GlcNAc=N-Acetylglucosamine; NeuAc=sialic acid; Sulfo=sulfate ester; T-hapten=Galβ1,3GalNAcα

The present invention is based on a surprising finding that mammalian sialyltransferase ST3Gal-II, in addition to forward sialylation, can also catalyze reverse sialylation under appropriate conditions. Our results indicate this enzyme is able to synthesize CMP-NeuAc by transferring NeuAc from the NeuAcα2,3Galβ1,3GalNAcα-unit of O-glycans, 3-sialyl globo unit of glycolipids and sialylated macromolecules to 5'-CMP. Thus, in one embodiment the present invention provides a method comprising the steps of providing a source of sialic acid (SA), providing a 5'-nucleotide monophosphate (5'-NMP), combining source of SA and the 5' NMP in the presence of a catalytic amount of ST3Gal-II to form SA-NMP.

The newly synthesized NMP-SA, e.g. CMP-NeuAc, can be utilized by the same enzyme to sialylate other O-glycans. This NMP-SA is also available for use by other sialyltransferases including ST6Gal-I and ST6GalNAc-I, and this results in α2,3 or α2,6 linkages on the new compounds. Besides using 5'-CMP as acceptor, ST3Gal-II can also catalyze the conversion of other 5'-nucleotide monophosphates. For example, it can catalyze the conversion of 5'-UMP to UMP-NeuAc. Reverse sialylation proceeds without the need for free sialic acid, divalent metal ions or CTP. It exhibits a sharp optimum at pH 5.6 in contrast to the wide pH optimum 5.2-7.2 in the case of direct sialylation (forward reaction).

Therefore, in another embodiment, this invention provides a method for enzymatic synthesis of diverse sialyl products by using the reverse sialyltransferase reaction. The method comprises providing a target glycoprotein, providing a SA-donor (such as SA-NMP), admixing the target glycoprotein and the SA-donor in a reaction mixture in the presence of sialyltransferase to form sialylated glycoprotein. The SA donor may carry a labeled SA so that the sialylated target glycoprotein can become detectably labeled. Detectable labels include radioisotopes (such as $^3$H and $^{14}$C) and fluorescent moieties.

Reverse sialylation is distinct from forward sialylation. Several properties distinguish forward/conventional vs. reverse sialylation: i) sodium citrate inhibits forward sialylation but not reverse sialylation; ii) 5'-CDP, a potent forward sialyltransferase inhibitor, does not inhibit the conversion of 5'-CMP to CMP-NeuAc; and, iii.) the mucin core 2 compound 3-O-sulfoα2,3Galβ1,4GlcNAcβ1,6(Galβ1,3)GalNAcα-O-Bn, an acceptor that can be efficiently sialylated by ST3Gal-II, inhibited the conversion of 5'-CMP to CMP-NeuAc via the reverse sialylation mechanism.

DESCRIPTION OF THE INVENTION

Figure 1:
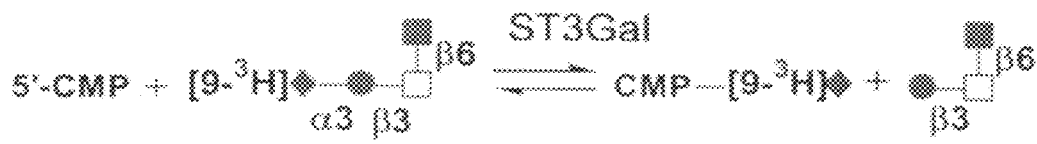
FIG. 1. Nucleotide phosphates as acceptors of radioactivity from [9-$^3$H]NeuAcα2,3Galβ,13 (GlcNAcβ1,6)GalNAcα-O—Al (Al=Allyl) [[9-$^3$H] [1]] in the presence of ST3Gal-II (scheme-I). Reaction mixtures (RM) with the following composition were incubated at 37° C. for 21 hours in 100 mM NaCa Codylate buffer, pH6.0: i) RM containing 150 μM (0.4 μCi) [[9-$^3$H] [1]] (donor) along with 0.8 mU ST3Gal-II but no 5''-CMP; and, ii) RM containing [[9-$^3$H] [1]] and 1.0 mM 5'-CMP, along with ST3Gal-II. Products formed were fractionated on a WGA-agarose column. Bound products were released using 0.5M GlcNAc at fraction 12. The radioactive product formed in ii) does not bind WGA. Thus, the forward reaction of scheme-I occurs at an appreciable rate. The feasibility of the reverse reaction is well established in literature. Schematic symbols: ♦:sialic acid, ●:Gal, ☐:GalNAc, ■:GlcNAc.
Figure 1:
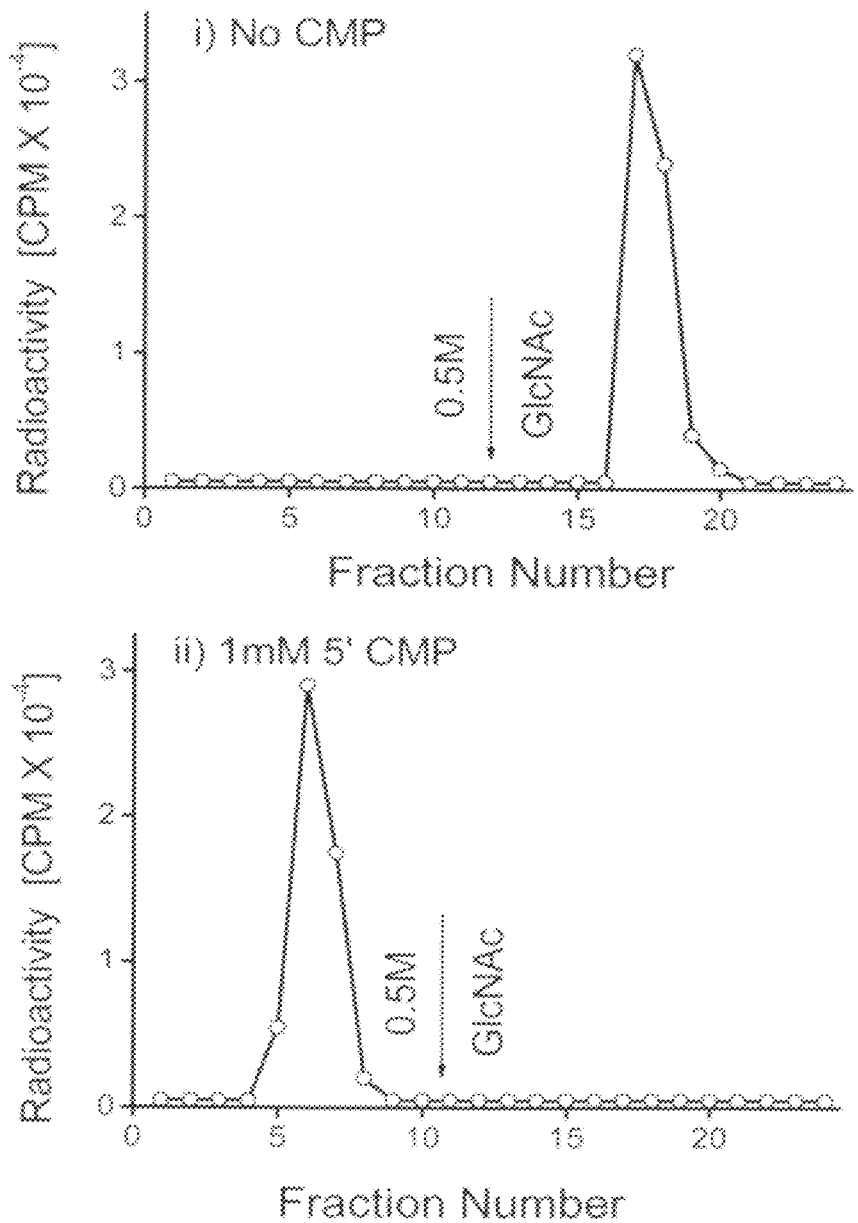

The present invention is based on the identification of a novel enzymatic reaction mechanism which we term "reverse sialylation". This reaction is observed to be catalyzed by mammalian ST3Gal-II. The reaction mechanism is not known, since the reversibility of sialyltransferase activity has not been reported in literature.

The incorporation of sialic acid into a molecule, which is an asialo glycoprotein, can be carried out using an enzyme, sialyltransferase, to catalyze the formation of glycosidic bond between sialic acid and asialo glycoprotein using a sialic acid donor (e.g. a sialylated nucleotide monophosphate (SA-NMP)). This is forward sialylation. In contrast, reverse sialylation is the enzymatic catalysis of a transfer of a sialic acid group from a source of sialic acid (a donor), e.g. a sialylated mucin glycoprotein, to an NMP to form a sialylated NMP or to an asialo glycoprotein acceptor to form a sialylated glycoprotein.

Reverse sialylation activity was observed to be exhibited by rat ST3Gal-II and lysates of human prostate cancer cell lines. Of the three enzymes studied (ST3Gal-II, ST3Gal-III and ST6Gal-I), reversible sialylation is observed to occur readily in the case of ST3Gal-II. The enzyme is a macromolecular catalyst and so it is needed in less than 1 microgram level to carry out reaction in milligram quantities for reverse sialylation reactions.

In one embodiment of the invention, the reverse sialylation reaction can be used to catalyze the formation of Nucleotide-NeuAc (NMP-NeuAc) in the presence of 5'-NMP and a NeuAc donor. The invention provides a method of sialylating 5'-cytidine monophosphate comprising the steps of admixing in a vessel the following components to form a reaction mixture: a) a source of sialic acid (natural or synthetic); b) 5'-cytidine monophosphate (CMP); and c) a catalytic amount of mammalian ST3Gal-II sialyltransferase, under conditions such that sialic acid-NMP is formed in the reaction mixture. While specific examples may refer to CMP-NeuAc (as illustrated in scheme-I), the invention is not limited to this NMP-NeuAc. For example, in addition to transfer of NeuAc to 5'-CMP using an array of donors, this enzyme activity also transfers sialic acid to 5'-UMP as well as other 5'-NMPs (see examples in Table II). Some of the NMP-NeuAc may not be as efficient sialyl donors as CMP-NeuAc. For example, the newly synthesized UMP-NeuAc, however, was observed to be a poor sialyl donor and thus formation of UMP-NeuAc can be used as a method for depleting sialyl donors.

Reverse sialylation can be used for the development of a glycoconjugate synthetic scheme. For example, because ST3Gal-II readily exchanges sialic acid residues between CMP-NeuAc and the α2,3-sialyl T-hapten unit, such a reaction can provide a rapid scheme for the synthesis of NeuAc analogs. In such reactions, addition of CMP-NeuAc analogs to mucin glycoproteins containing α2,3-sialyl T-hapten units in the presence of ST3Gal-II can catalyze the formation of modified T-hapten units. Further, if one considers the high cost of CMP-sialic acid and because fetuin (a glycoprotein containing sialylated O-glycan chains) is commercially available and is relatively inexpensive, the synthesis of CMP-sialic acid using CMP and ST3Gal-II using the sialyl donor fetuin appears to be an alternative approach in the in situ production of CMP-sialic acid for an economical synthesis of sialyl oligosaccharides.

To obtain CMP-NeuAc by the reverse sialylation reaction a range of donors containing NeuAcα2,3Galβ1,3GalNAc-can be used. Examples of suitable donors include sialic acid containing glycoproteins and glycolipids, and sialylated macromolecule structures. The glycoproteins can be mucin core-2 glycoproteins, mucin core-1 glycoprotein, fetuin, and the like. The glycolipids can be gangliosides.

Figure 10:
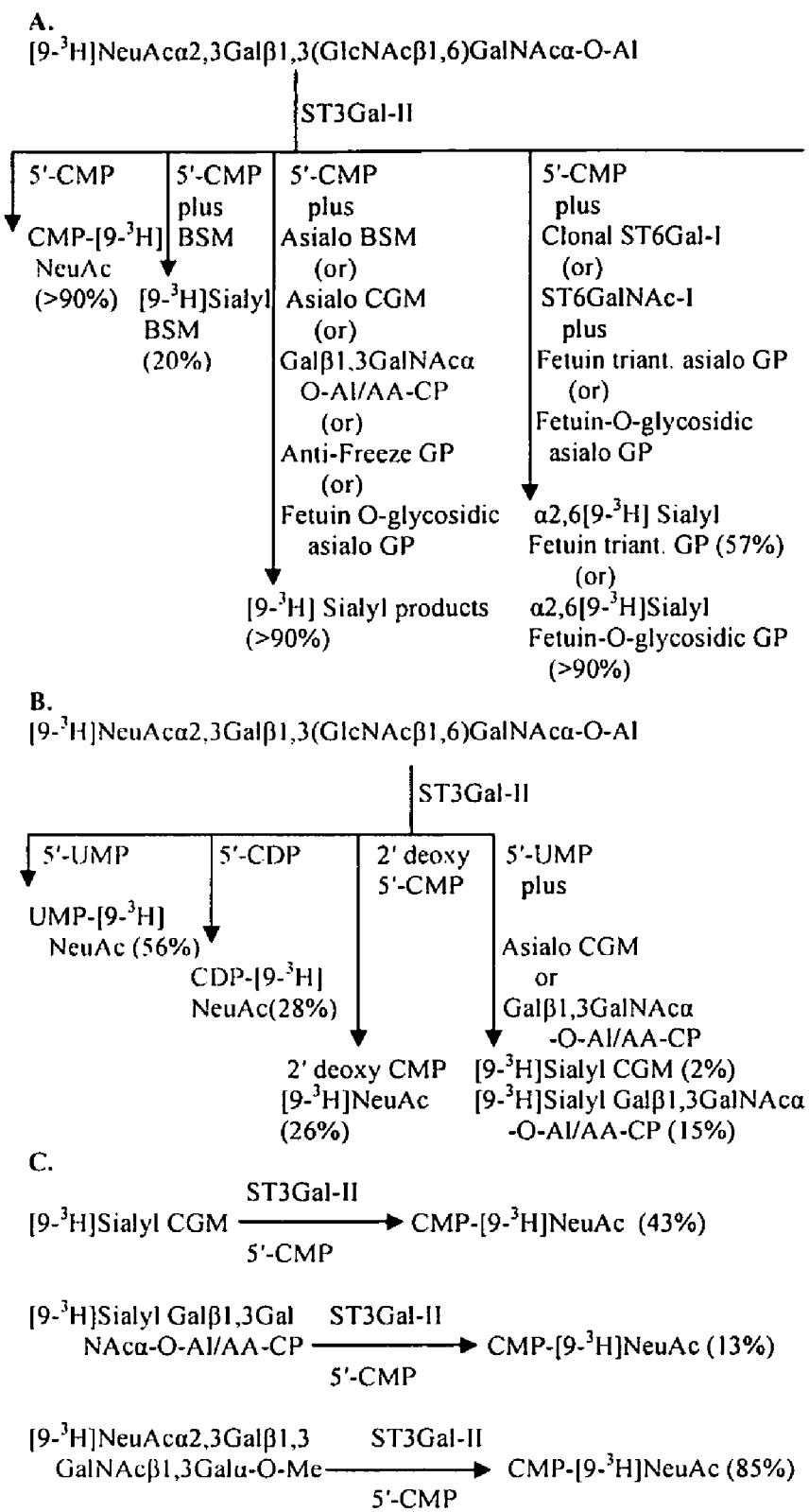
FIG. 10. Summary of reactions studied in this invention.

NMP-NeuAcs, such as CMP-NeuAc, formed by reverse sialylation above are available for transfer to a range of substrates using sialylTs that catalyze both α2,3 and α2,6 linkage formation. Enzymes that catalyze forward sialylation using CMP-NeuAc formed by reverse sialylation as donor to other non-sialylated acceptors include ST3Gal-II, ST6Gal-I and ST6GlcNAc-I. Together these observations indicate that the reversible sialylation function of ST3Gal-II can be used for the synthesis of sialylated glycoconjugates. FIG. 10 summarizes the reactions described herein, and this includes a list of examples of some of the sialylated compounds formed using reverse sialylation.

The requirements for the formation of CMP-NeuAc using reverse sialylation activity are unlike that of forward CMP-NeuAc synthetase function that utilizes CTP and NeuAc as substrates in the presence of $Mg^{2+}$ to produce CMP-NeuAc and pyrophosphate. In contrast, reverse sialylation involves the direct transfer of NeuAc to 5'-CMP proceeded without the need of free sialic acid, divalent metal ions or energy from the breakdown of cytidine triphosphate (CTP) to CMP and pyrophosphate. Thus, the reverse sialylation is favored under conditions that are distinct from conditions that favor the forward sialylation reaction. For example, a condition favoring reverse sialylation is when the pH of the reaction mixture is 5.0 to 6.0, and preferably from 5.5 to 5.7, and more preferably 5.6.

Without intending to be bound by any particular theory, our data suggest that direct/forward sialylation and reverse sialylation by ST3Gal-II may be governed by two distinct catalytic mechanisms. In this regard, we noted that reverse and forward sialylation are optimum at different, albeit overlapping, pH ranges. While direct/forward sialylation using ST3Gal-II was optimum over a wide pH range from 5.2 to 7.2, the formation of CMP-NeuAc from 5'-CMP by reverse sialylation occurred between 4.8 and 6.4. Because of these two different pH activities, the two step reaction scheme shown in Scheme-II exhibited a sharp peak at a pH of 5.6. In support of this proposition, we have also found that: i) while strong inhibition of sialyltransferase activity occurs upon addition of sodium citrate, reverse sialylation (namely the formation CMP-NeuAc from 5'-CMP) was not inhibited by citrate; ii) we also observed that while 5'-CDP was a potent inhibitor of direct/forward sialyltransferase activities, it did not affect the synthesis of CMP-NeuAc from 5'-CMP in the reverse sialylation reaction mediated by ST3Gal-II; and iii) while the mucin core 2 compound 3-O-sulfoGalβ1,4GlcNAcβ1,6(Galβ1,3)GalNAcα-O-Bn inhibited the conversion of 5'-CMP to CMP-NeuAc via the reverse sialylation mechanism, the corresponding α2,3-sialyl substituent NeuAcα2,3 Galβ1,4GlcNAcβ1,6(Galβ1,3)GalNAcα-O-Bn did not inhibit reverse sialylation. Also, in previous studies, we showed that NeuAcα2,3Galβ1,4 GlcNAcβ1,6(Galβ1,3)GalNAcα-O-Bn was a poor acceptor for ST3Gal-II compared to 3-O-sulfoGalβ1,4GlcNAcβ1,6 (Galβ1,3)GalNAcα-O-Bn. Thus, the latter acceptor 3-O-sulfoGalβ1,4GlcNAcβ1,6(Galβ1,3)GalNAcα-O-Bn can be sialylated by ST3Gal-II and it simultaneously inhibits the reverse sialylation process. Taken together the data suggest that forward and reverse sialylation follow different reaction coordinates and that the enzyme ST3Gal-II may have more than one catalytic activity. Because forward and reverse sialylation can be independently regulated using citrate ions, 5'-CDP and selected synthetic molecules, it is possible the two distinct catalytic activities of the enzyme regulate the forward and reverse sialylation reactions.

In another embodiment, the activity we term "reversible sialylation" involves the enzymatic transfer of NeuAc by mammalian sialylT ST3Gal-II, from glycoprotein and glycolipid based sialylated donors (natural or synthetic) to acceptor glycoproteins and glycolipids. This results in the formation of sialylated glycoconjugates. The present invention provides a method for sialylating an acceptor glycoprotein or glycolipid comprising the steps of admixing in a vessel the following components to form a reaction mixture: a) a sialic acid donor other than sialic acid-NMP; b) an acceptor glycoprotein or glycolipid (either of which can be natural or synthetic); and c) catalytic amount of mammalian ST3Gal-II sialyltransferase, under conditions such that a sialylated acceptor glycoprotein is formed in the reaction mixture.

To obtain sialylated glycoproteins by the reverse sialylation reaction a range of donors containing NeuAcα2,3Galβ1, 3GalNAc- can be used. Examples of suitable donors include sialic acid containing glycoproteins and glycolipids, and sialylated macromolecule structures. The glycoproteins include mucin core-2 glycoproteins, mucin core-1 glycoprotein, fetuin. The glycolipids include gangliosides.

In yet another embodiment, the SA donor may carry a labeled SA so that the sialylated target glycoprotein can become detectably labeled. Detectable labels include radioisotopes (such as $^3$H and $^{14}$C) and fluorescent moieties.

Non-limiting uses of the present invention include: radiolabeling CD43, human chorionic gonadotrophin B, MN Glycophorin-A, GlyCAM-I through enzymatic exchange of sialyl residues and then characterization; radiolabeling of fetuin, human placental glycoproteins, bovine casein macroglycopeptide and porcine Cowper's gland mucin and then characterization; radiolabeling of cellular glycoproteins in cell lysates from some human cancer cell lines and then characterization; and radiolabeling of tumor glycoproteins and then characterization.

The following examples are presented to illustrate the invention and are not intended to be restrictive in any way.

Example 1

Materials and Methods

Materials

Rat recombinant ST3Gal-II (α2,3(O)ST), ST3Gal-III (α2, 3(N)ST) and ST6Gal-I (α2,6(N)ST) were purchased from Calbiochem. Several different lots of ST3Gal-II have been used for this study and all yielded similar findings. Cloned ST6GalNAc-I (chicken) was kindly provided by Dr. James C. Paulson (Scripps Research Institute, La Jolla, Calif.). All nucleotide phosphates and CMP-NeuAc were from Sigma. Preparation of acrylamide copolymer of Galβ1,3GalNAcα-O—Al, asialo Cowper's gland mucin (CGM), Anti-Freeze glycoproteins, Fetuin-O-glycosidic asialo glycopeptide (asialo FOG) and Fetuin Triantennary asialo Glycopeptide (asialo FTG) is known in the art. The culturing of human cancer cell lines and the preparation of cell extracts was according to known methods. All cell extracts were frozen at −20° C. prior to use. Asialo bovine submaxillary mucin (asialo BSM) was made by heating BSM (Sigma) (5 mg/ml) at 80° C. in 0.1N HCl for 1 h, neutralizing with 1.0N NaOH, dialyzing against distilled deionized water in the cold room for 24 h with four changes and then lyophilizing the product.

Enzymology Studies

All enzymatic sialylation reactions were typically carried out in 100 mM NaCa Codylate buffer pH6.0 in the presence of enzyme, synthetic acceptor (at 7.5 mM or as indicated in each experiment) and 0.2 μCi CMP-[9-$^3$H]NeuAc (NEN-Dupont, 29 mCi/μmol). The concentration of total CMP-NeuAc was adjusted in individual reactions by supplementing with additional cold CMP-NeuAc. Reaction volume was 20 μl. Products formed were separated using four different chromatography procedures (below). In all cases, the radioactive content of isolated products was determined by using 3a70 scintillation cocktail (Research Products International, Mount Prospect, Ill.), and a Beckman LS6500 scintillation counter.

a) Biogel P2 chromatography: A Biogel P2 column (Fine Mesh; 1.0×116.0 cm) was used with 0.1 M pyridine acetate (pH5.4) as the eluent at room temperature. In cases where radiolabeled donor compounds were prepared using this column, the peak fraction containing radioactivity was collected, lyophilized to dryness, dissolved in small volume of water and stored frozen at −20° C. for further experimentation.

b) Lectin-agarose affinity chromatography: A column of 5 ml bed volume of WGA-agarose or PNA-agarose (Vector Lab, Burlingame, Calif.) was employed using 10 mM Hepes pH7.5 containing 0.1 mM CaCl$_2$, 0.01 mM MnCl$_2$ and 0.1% NaN$_3$ as the running buffer. Fractions of 1.0 ml were collected. The bound material was then eluted with 0.5M GlcNAc or 0.2M Gal in the same buffer. SNA-agarose (Vector Lab) affinity chromatography was also carried out as above except that fractions of 2.0 ml were collected and the bound material was eluted with 0.5M lactose.

c) Hydrophobic chromatography: This was done using Sep-Pak C18 cartridge (Waters, Milford, Mass.) and eluting the product with 3.0 ml methanol.

d) Dowex-1-Formate column: Radioactive products from neutral allyl and methyl glycosides were measured by fractionation on Dowex-1-Formate (Bio-Rad:AG-1×8; 200-400 mesh; format form) (10).

Calculation of equilibrium constant, Keq: Equilibrium constant was calculated for selected reversible bimolecular reactions that are denoted by:

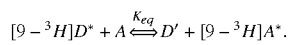

$$[9-{}^3H]D^* + A \overset{K_{eq}}{\Longleftrightarrow} D' + [9-{}^3H]A^*.$$

Here, $[9-{}^3H]D^*$ denotes the radiolabeled donor and D' is the donor after removal of sialic acid. Similarly, A and $[9-{}^3H]A^*$ denote the acceptor before and after incorporation of NeuAc. In each run, unreacted $[9-{}^3H]D^*$ and product $[9-{}^3H]$ $A^*$ are measured using radioactivity measurements. The equilibrium constant ($K_{eq}=k_{reverse}/k_{forward}$, dimensionless units) are then determined using the following equation, where terms in square brackets denote concentrations:

$$K_{eq} = \frac{[D^*][A]}{[D'][A^*]} = \frac{[D^*]}{([D_0]-[D^*])} \cdot \frac{([A_0]-[A^*])}{[A^*]}$$

$[D_0]$ and $[A_0]$ are initial donor and acceptor concentrations. A plot of $[D^*]/([D_0]-[D^*])$ versus $[A^*]/([A_0]-[A^*])$ yields $K_{eq}$ from slope data. $K_{eq}<1$ implies that the forward reaction is favored and the reaction proceeds to the right side to form $[9-{}^3H]A^*$ efficiently.

Liquid Chromatography Coupled with Tandem Mass Spectrometry (LC/MS/MS)

The LC separation was performed using a C18 reverse phase column at a flow rate of 220 μL/minute. Two buffers, 0.1% formic acid in acetonitrile and 0.1% formic acid in water were used, with a linear gradient of 8%/min increase of the organic buffer starting from 20%. The sample injection volume was 20 μL. Negative-ion ESI was used for the detection of sialic acid derivatives due to its superior sensitivity to positive-ion ESI. The identification was accomplished in precursor ion scan mode at unit resolution (FWHM 0.6-0.8 amu) by selectively detecting the parent ions in the third quadrupole (Q3) of a triple quadrupole instrument that give rise to the diagnostic fragment ion (sialic acid ion [M-H]⁻ at m/z 290) created by collisions in the second quadrupole (Q2).

Results

ST3Gal-II Reverse Sialylates 5'-CMP

Cloned and purified rat sialyltransferase α2,3(O)ST (ST3Gal-II) is used in many experiments presented in this manuscript. This enzyme has been shown to mediate α2,3 sialylation of terminal Gal residues in the O-glycan core-2 trisaccharide unit Galβ1,3(GlcNAcβ1,6)GalNAcα. In order to determine if the sialylation reaction is reversible (FIG. 1), [9-³H]NeuAcα2,3Galβ,13(GlcNAcβ1,6)GalNAcα-O—Al (Al=Allyl) [9-³H[1]] was prepared using ST3Gal-II in the presence of CMP-[9-³H]NeuAc and the trisaccharide acceptor Galβ1,3(GlcNAcβ1,6)GalNAcα-O—Al, and the radiolabeled product was isolated using Biogel P2 chromatography. During this isolation, radiolabeled [9-³H[1]] appeared prior to unreacted trisaccharide (data not shown). Two different reaction mixtures were then prepared with: i) [9-³H[1]] and ST3Gal-II but without 5"-CMP; and ii) [9-³H[1]] and 5"-CMP along with ST3Gal-II. When the products formed were subjected to WGA-agarose affinity chromatography, a majority of the radioactive component from i) but not ii) bound the column (FIG. 1). The results of the first run indicate that the enzyme ST3Gal-II does not exhibit any sialidase activity. Further, the efficient (>90%) transfer of radioactive [9-³H]NeuAc from 150 μM [9-³H[1]] to 1.0 mM 5'-CMP in the presence of ST3Gal-II in the second panel suggests that the reverse reaction in scheme-I proceeds at an appreciable rate.

Figure 2:
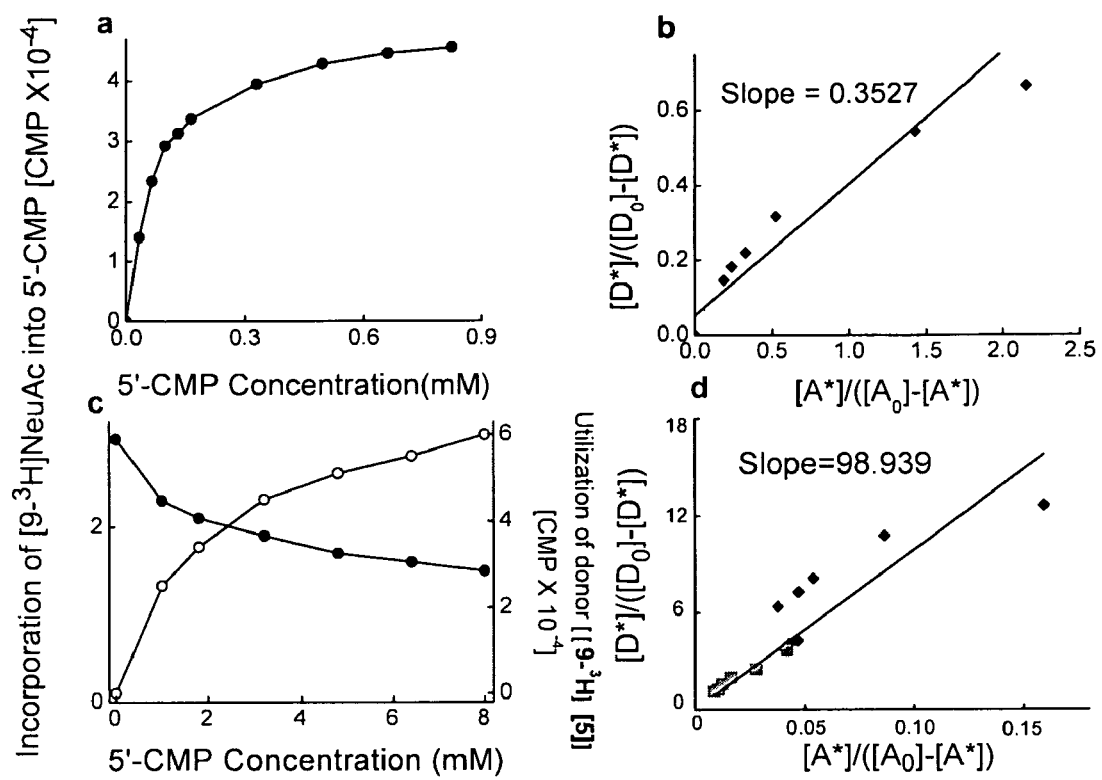
FIG. 2. Equilibrium constant. a. Reversible sialyltransferase activity at increasing concentration of 5'-CMP. 0.15 mM of donor [9-$^3$H]NeuAcα2,3Galβ1,3(4-FGlcNAcβ1,6)GalNAcα-O-Bn [9-$^3$H[2]] was incubated with varying concentrations of 5'-CMP and 0.15 mU ST3Gal-II under conditions described in FIG. 1 for 2 hours. The consumption of the [9-$^3$H]NeuAc benzyl glycoside donor was measured by subjecting the incubation mixture to Sep-Pak C18 fractionation, which binds the donor and not CMP-[9-$^3$H]NeuAc. The reaction proceeded to ½ the maximum extent at 80 μM 5'-CMP. b. Equilibrium constant $K_{eq}$ (=0.35) calculated for data in panel a. c. Varying concentrations of 5'-CMP was sialylated with ST3Gal-II (2.0 mU) using either 0.15 mM (panel c) or 1.5 mM (not shown) sialyl donor [9-$^3$H]NeuAcα2,3Galβ1,3GalNAcβ1,3Galα-O-Me [9-$^3$H[3]] for 4 hours. The product CMP-[9-$^3$H]NeuAc and the unused [9-$^3$H[3]] were separated and quantitated by Dowex-1-Formate method. d. Equilibrium constant, $K_{eq}$=98.9. Diamonds denote data from 1.5 mM runs while data from 0.15 mM runs are depicted by squares.

Similar results were observed upon increasing concentrations of 5'-CMP when [9-³H]NeuAcα2,3Galβ1,3(4-FGlcNAcβ1,6) GalNAcα-O-Bn [9-³H[2]] was donor (FIG. 2a, b). The concentration of 5'-CMP that mediated half-maximal transfer of [9-³H]NeuAc was 80 μM. The bimolecular equilibrium constant ($K_{eq}$) for this reaction was 0.35 (dimensionless units, Table I). Indeed, the $K_{eq}$ varied depending on the donor and it was 98.9 when the donor was based on the globo glycolipid, [9-³H]NeuAcα2,3Galβ1,3GalNAcβ1,3 Galα-O-Me [[9-³H] [3]] (FIG. 2c, d). Upon comparing [2] and [3], it is apparent that reverse sialylation proceeds more effectively in the case of [2]. To further confirm the above estimates of $K_{eq}$ for core-2 based structures, we also calculated this parameter for our previously published data where [9-³H]CMP-NeuAc was donor and mucin core-2 tetrasaccharide Galβ1,4GlcNAcβ1,6(Galβ1,3)GalNAcα-O-Bn was acceptor. In this case, $K_{eq}$ measured with respect to the rate of mucin core-2 sialylation was 5.55 (data not shown), which translates to a reverse sialylation $K_{eq}$ of 0.18. Table I provides a summary of $K_{eq}$ values for reverse sialylation.

Figure 11:
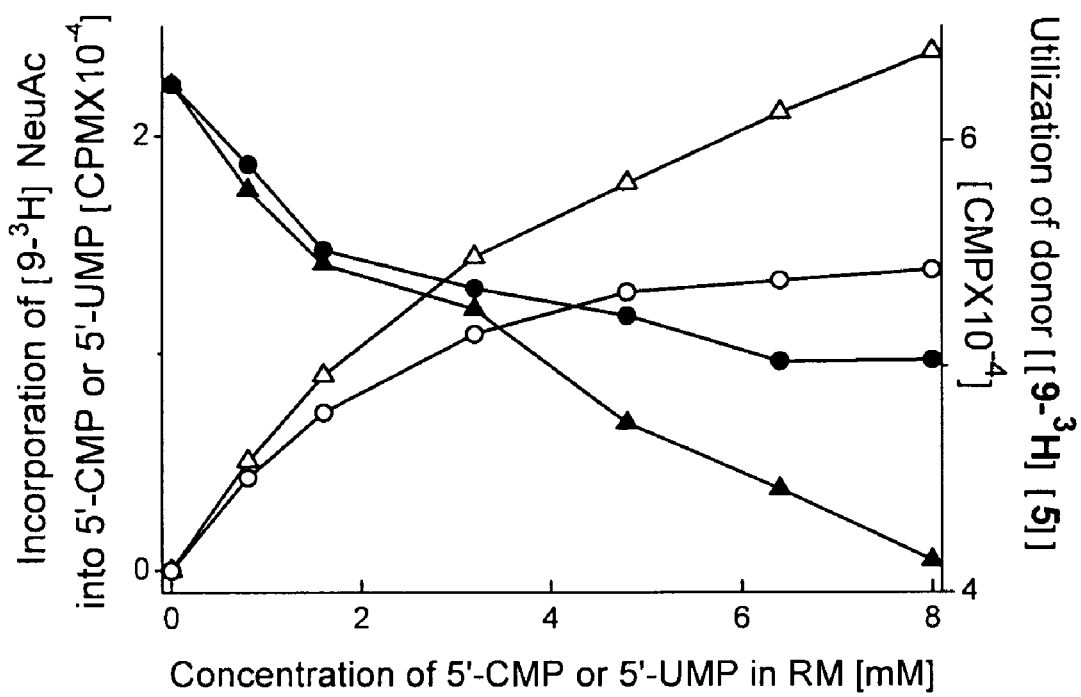
FIG. 11. Varying concentrations of 5'-CMP or 5'-UMP were sialylated with ST3Gal-II (2.0 mU) using 0.25 mM sialyl donor [9-$^3$H[3]] for 4 h at 37° C. The product CMP-[9-3H]NeuAc or UMP-[9-$^3$H]NeuAc and the unused [9-$^3$H[3]] were separated and quantitated by Dowex-1-Formate method. ☐ Formation of CMP-[9-$^3$H]NeuAc; ▲Utilization of [9-$^3$H[3]] by 5'-CMP; ○ Formation of UMP-[9-$^3$H] NeuAc; ● Utilization of [9-$^3$H[3]] by 5'-UMP.

When other nucleotide phosphates were substituted for 5'-CMP, their effectiveness varied (Table II). 5'-UMP, 5'-CDP and 2'deoxy 5'-CMP were 55.9%, 28.4% and 26.3% effective in comparison with 5'-CMP. Dosage studies further confirm the formation of UMP-NeuAc via the reverse sialylation mechanism (FIG. 11). In these studies where [9-³H[3]] was donor and 5'-CMP or 5'-UMP was acceptor, CMP-[9-³H] NeuAc was observed to form more efficiently than UMP-[9-³H]NeuAc. Other nucleotide phosphates had lower activity (Table II). 5'-CMP in the presence of cold sialic acid did not show any decrease in accepting [9-³H]NeuAc from donor (100.3%), indicating that reverse sialylation did not involve the formation of free sialic acid as intermediate. Such free sialic acid could be formed following hydrolysis of donor. Overall, the data support the reverse sialylation mechanism shown in scheme-I.

ST3Gal-II Utilizes CMP-NeuAc Formed in Reverse Reaction to Sialylate O-Glycans

Figure 3:
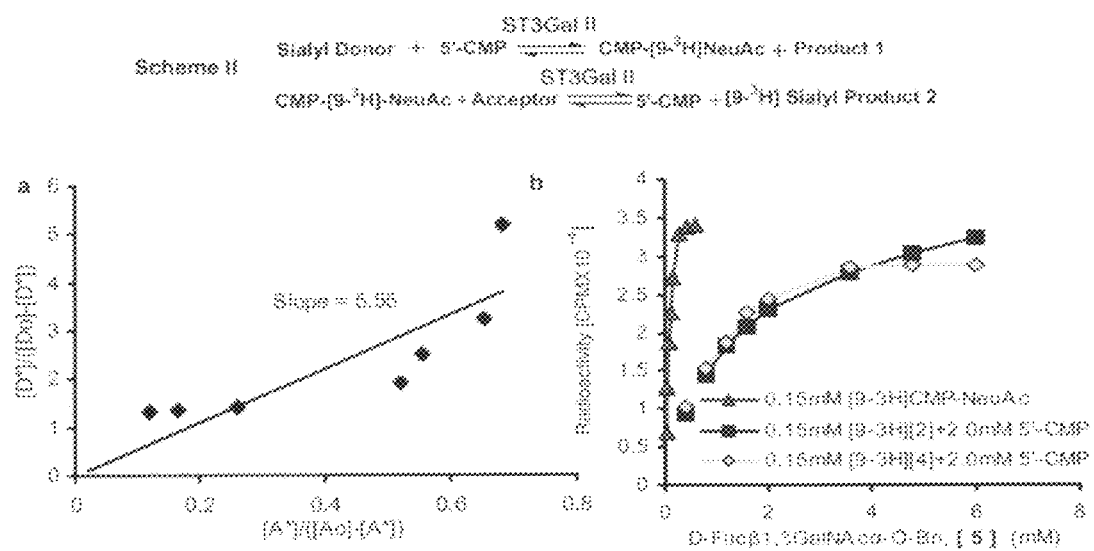
FIG. 3. Serial transfer of sialic acid using scheme-II was followed at increasing concentrations of acceptor D-Fucβ1,3GalNAcα-O-Bn [5]. The donor used was either: i) 0.15 mM [9-$^3$H]CMP-NeuAc; or, ii) 0.15 mM [9-$^3$H]NeuAcα2, 3Galβ1,3(4-FGlcNAcβ1,6)GalNAcα-O-Bn [9-³H [2]] in the presence of 2.0 mM 5'-CMP, or iii) [9-³H]NeuAcα2,3Galβ1, 3(6-O-SulfoGlcNAcβ1,6)GalNAcα-O—Al [[9-³H] [4]] in the presence of 2.0 mM 5'-CMP. In runs where [9-³H [2]] was donor since both [5] and [2] bind C18 cartridges, control runs were performed in the absence of D-Fucβ1,3GalNAcα-O-Bn to estimate the amount of [9-³H]CMP-NeuAc formed under the experimental conditions. 80-85% of the radioactivity was transferred to CMP-NeuAc in these runs. The amount of CMP-NeuAc remaining in runs with [5] was then subtracted from CMP-NeuAc radioactivity in the control run to determine the amount of sialylated [5]. To complement this run, studies were also performed with [[9-³H] [4]], a molecule with Allyl at the anomeric position, which does not bind C18. In these runs, the amount of sialylated [5] was determined by measuring radioactivity retained in the C18-cartridge. a. Equilibrium constant was 5.55 when CMP-[9-³H]NeuAc was donor. b. ~10-fold lower acceptor concentration was required for similar extents of reaction when CMP-[9-³H]NeuAc was donor, compared to core-2 based donors [2] and [4].

We tested the possibility that CMP-NeuAc formed above may be available for transfer to other acceptors using ST3Gal-II (scheme-II, FIG. 3). For this, three radiolabeled donors were prepared using methods described above: two were based on the mucin Core-2 structure ([[9-³H] [1]] and [9-³H]NeuAcα2,3Galβ1,3(6-O-SulfoGlcNAcβ1,6)Gal-NAcα-O—Al [[9-³H] [4]]) while the third was based on the Globo glycolipid ([9-³H] [3]). The transfer of [9-³H]NeuAc from these sialylated donors to various T-hapten (Galβ1, 3GalNAcα) and mucin core2-based glycoside acceptors in the presence of 5'-CMP and ST3Gal-II was assessed (Table III). All three acceptors of ST3Gal-II ([1], [3] and [4]) allowed formation of CMP-[9-³H]NeuAc, and a diverse array of products. In contrast to this, two other molecules ([9-³H] NeuAcα2,3Galβ1,4GlcNAcβ-O—Al and [9-³H]NeuAcα2, 6Galβ1,4GlcNAcβ-O—Al), which were formed by sialylation of a poor acceptor of Gal3ST-II (Galβ1,4GlcNAcβ-O—Al) by enzymes ST3Gal-III and ST6Gal-I, did not act as donors in the reverse sialylation reaction (see discussion of Table IV, next section). Thus, while the reversible function of ST3Gal-II is not unique to a given donor-acceptor pair, products of donors that are good acceptors of ST3Gal-II are more efficient substrates for reverse sialylation. In addition, as seen in Table I, α2,3 sialic acid linkage on different substrates have vastly different $K_{eq}$ values.

Figure 12:
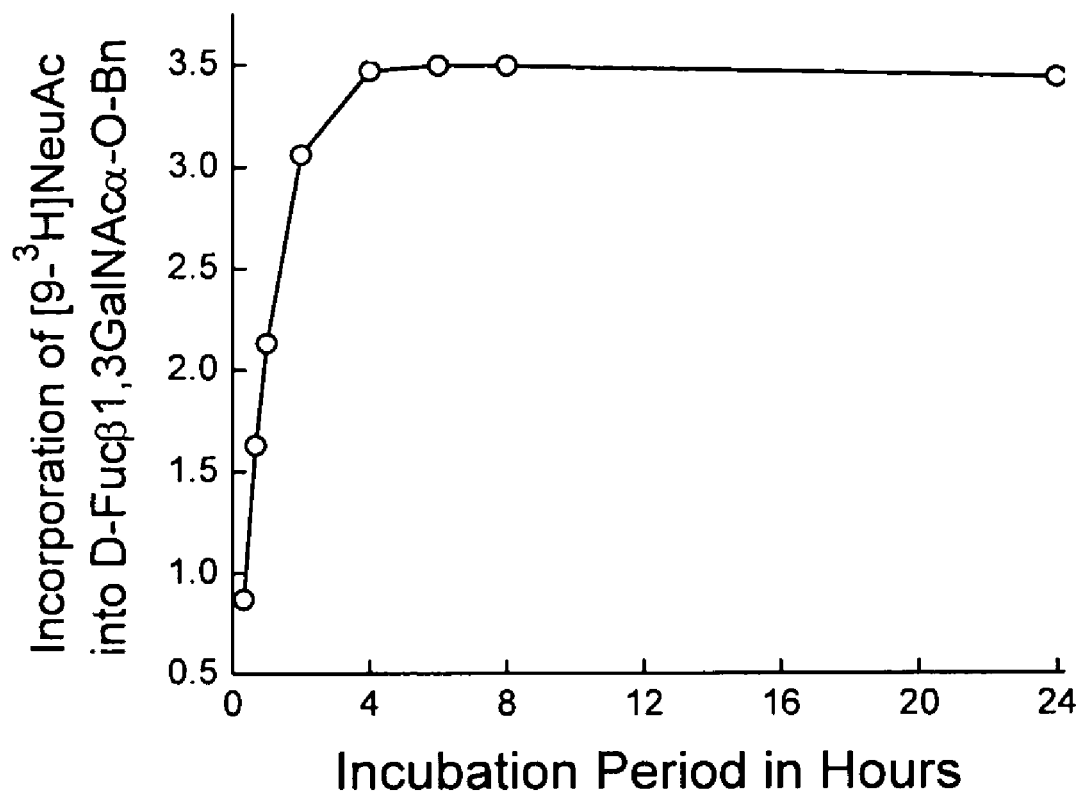
FIG. 12. Reversible sialyltransferase activity at different incubation periods. The transfer of [9-$^3$H]NeuAc from 0.15 mM [[9-$^3$H[1]] to 2.5 mM D-Fucβ1,3GalNAc α-O-Bn [5] in the presence of 0.8 mM 5'-CMP and 0.5 mU ST3Gal-II was studied at 37° C. for varying times using Sep-Pak C18 method. The reaction reached equilibrium by 4 hours.

The transfer of [9-$^3$H]NeuAc from [[9-$^3$H][1]] to D-Fucβ1, 3GalNAcα-O-Bn [5] in the presence of 5'-CMP and ST3Gal-II increased linearly in the first two hours and it reached saturation at 4 hours (FIG. 12), and thus the data in Table III (4 hours time point) represent equilibrium conditions. In Table III, [5] and D-Fucβ1,3(GlcNAcβ1,6)GalNAcα-O-Bn [6] were observed to serve as good acceptors followed by 4-FGalβ1,3GalNAcα-O-Bn [7] and Galβ1,3(6-O-Me)GalNAcα-O-Bn [8], while 4-O-methylation of β1,3-linked Gal [11] reduced acceptor efficiency. As anticipated, Galβ1, 4GlcNAcβ-O-Bn [12] was an inactive acceptor since ST3Gal-II does not act on it. Because CMP-NeuAc is formed via the same first reaction of scheme-II for a given donor, the data in Table III suggest that acceptor specificity for ST3Gal-II may govern the extent of reaction. Further, diverse sialylated products can be formed using the same synthetic sialylated donor.

In order to compare the efficiency of individual reactions of scheme II, independent runs were performed where either 0.15 mM [9-$^3$H]CMP-NeuAc, 0.15 mM [9-$^3$H] [2] or 0.15 mM [9-$^3$H] [4] was the donor, and [5] was the acceptor (FIG. 3). 2 mM 5'-CMP was added in runs with core-2 donors [2] and [4], and thus reverse sialylation of these molecules was feasible. $K_{eq}$ for transfer of sialic acid from CMP-NeuAc to [5] was 5.55 (FIG. 3a). As seen in FIG. 3b, 10-fold lower amounts of acceptor (0.6 mM [5]) was required for comparable transfer when CMP-NeuAc was donor versus the case where the donor was either [9-$^3$H [2]] (~6 mM) or [9-$^3$H[4]] (~6 mM). Thus, while the two-step mechanism results in lower conversion than CMP-NeuAc alone, the transfer of NeuAc still takes place at an appreciable rate.

Reverse Sialylation Occurs More Readily with ST3Gal-II Compared to ST3Gal-III and ST6Gal-I We determined if reverse sialylation was more pronounced for ST3Gal-II in comparison to other sialyltransferases. Thus two other cloned rat sialyltransferases ST3Gal-III (or α2,3 (N)ST) and ST6Gal-I (or α2,6(N)ST) (14) were examined. For these studies, we generated two molecules: i) [9-$^3$H] NeuAcα2,6Galβ1,4GlcNAcβ-O—Al (Al-Allyl) [14] was made by the reaction of Galβ1,4GlcNAcβ-O—Al and CMP-[9-$^3$H]NeuAc in the presence of α2,6sialyltransferase, ST6Gal-I. (The radioactive product was separated using Biogel P2 column using a protocol similar to that described above.); and ii) [9-$^3$H]NeuAcα2,3Galβ1,4 GlcNAcβ-O—Al [15] was similarly produced by reacting Galβ1,4GlcNAcβ-O—Al and CMP-[9-$^3$H]NeuAc in the presence of α2,3sialyltransferase ST3Gal-III. We note that the acceptor used in the above runs, Galβ1,4GlcNAcβ-O—Al, does not undergo significant sialylation in the presence of CMP-NeuAc and the sialyltransferase, ST3Gal-II. However, it is efficiently sialylated by both ST3Gal-III and ST6Gal-I. The ability of these two radiolabeled molecules ([14] and [15]) to act as [9-$^3$H] NeuAc donors was assayed in studies (Table IV) where the compounds were mixed with excess 5'-CMP, enzyme and acceptors with benzyl aglycan group. C18 cartridges were then used to measure the extent of [9-$^3$H]NeuAc transferred to acceptor using reaction scheme-II. Because all acceptors used in this table are efficiently sialylated by enzymes listed in the adjacent columns, these experiments essentially measure the amount of CMP-NeuAc formed using particular donor-enzyme pairs.

As seen in Table IV, the formation of CMP-NeuAc was negligible when either [9-$^3$H]NeuAcα2,6Galβ1,4GlcNAcβ-O—Al or [9-$^3$H]NeuAcα2,3Galβ1,4GlcNAcβ-O—Al was the donor in the presence of a series of acceptors and sialyltransferases ST6Gal-I and ST3Gal-III respectively. Thus, reverse sialylation takes place with ST3Gal-II. When these two radiolabeled donors were used in the presence of ST3Gal-II, also, we observed the formation of negligible amounts of product suggesting that CMP-NeuAc was not formed via reverse sialylation from these two donors. Thus, again, only products of donors that are good acceptors of a given enzyme may act as efficient substrates for reverse sialylation. While the possibility that ST3Gal-III and ST6Gal-I can mediate reverse sialylation under different conditions cannot be rules out based on the above studies, the data do suggest that ST3Gal-II may have unique structural properties that confer the reverse sialylation activity.

pH Dependence of Reverse Sialylation

Figure 4:
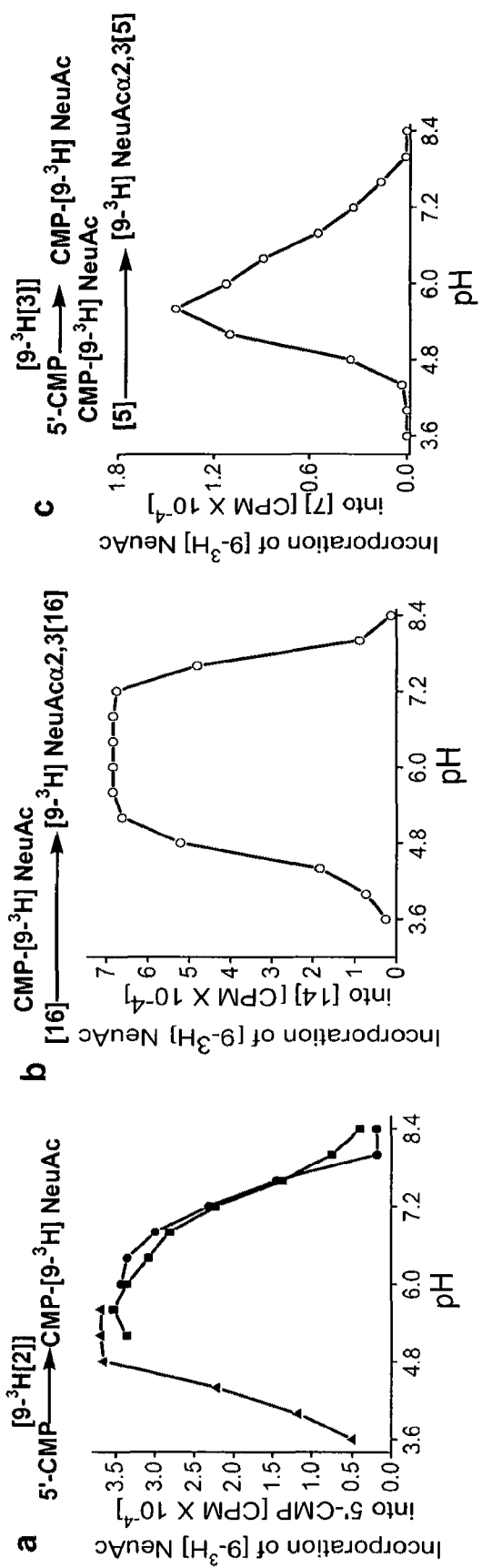
FIG. 4. Effect of pH on ST3Gal-II catalytic activity measured over a range of buffer pH using: Na acetate (▲, pH=3.6-5.6), Hepes-NaOH (●, pH=6.0-8.4) and Tris-Maleate (■) buffers: a. Sialylation of 5'-CMP (2.0 mM) by ST3Gal-II (0.15 mU) using donor [9-³H]NeuAcα2,3Galβ1,3(4-F-GlcNAc(31,6)GalNAcα-O-Bn [9-³H[2]] was optimum in pH range 4.8-6.4; b. Direct Sialylation of 1.0 mM Galβ1,3Gal-NAcα-O-Bn [16] by 0.15 mU ST3Gal-II using 0.1 mM [9-³H] CMP-NeuAc as donor was optimum in the pH range 5.2-7.2; and c. Reversible sialylation of 6.0 mM D-Fucβ1, 3GalNAcα-O-Bn [5] by 0.15 mU ST3Gal-II using the donor 0.15 mM [9-³H[3]] and 2.0 mM 5'-CMP displayed a sharp optimum at pH5.6. C18 cartridge was used to quantify extent of all reactions since compounds with benzyl group at anomeric position but not [9-³H]CMP-NeuAc binds C18. All reactions were carried out at 37° C. for 4 hours. In panels b and c Na acetate and Hepes-NaOH buffers were used respectively for pH3.6-5.6 and pH6.0-8.4.

We examined if the pH range in which ST3Gal-II catalyzes the formation of CMP-NeuAc from sialylated donor (first part of scheme-II) and the incorporation of this newly formed NeuAc into acceptor (second part) are distinct. First, in studies that measured the transfer of [9-$^3$H]NeuAc from donor [9-$^3$H[2]] to 5'-CMP, we observed optimum transfer at pH range 4.8-6.4 (FIG. 4a). In contrast, the transfer of [9-$^3$H] NeuAc from CMP-[9-$^3$H]NeuAc to Galβ1,3GalNAcα-O-Bn [16] was maximum at pH 5.2-7.2 (FIG. 4b). Due to these two distinct catalytic activities, the entire reaction scheme which was measured by monitoring the transfer of [9-$^3$H]NeuAc to [5] from the donor [9-$^3$H[3]] via 5'-CMP showed a sharp peak at pH 5.6 (FIG. 4c). The possibility that this enzyme may have multiple functions was studied in greater detail below.

Distinct Effects of Citrate on Forward and Reverse Sialyltransferase Activities

Besides pH other distinctions were also observed between forward and reverse sialylation. In this regard, citrate ions tended to inhibit forward sialylation but not reverse sialylation activity (Table V). For these studies, the effect of citrate on the forward sialylation activity of ST3Gal-I, ST3Gal-II, ST3Gal-III and ST6Gal-I was examined. Reverse sialylation activity of ST3Gal-II was also measured in terms of: i) the formation of CMP-NeuAc from 5'-CMP; and ii) the transfer of NeuAc from this newly synthesized CMP-NeuAc to another O-glycan. From the data (Table V), it is evident that citrate inhibits the direct sialylation activity of all the enzymes mentioned above. However, both the synthesis of CMP-[9-$^3$H]NeuAc from 5'-CMP as well as the synthesis of [9-$^3$H]NeuAcα2,3D-Fucβ1,3 GalNAcα-O-Bn using the newly formed CMP-[9-$^3$H]NeuAc through reverse sialylation of ST3Gal-II was not inhibited by citrate.

Effect of 5'-Nucleotides on Reverse Sialylation

Figure 5:
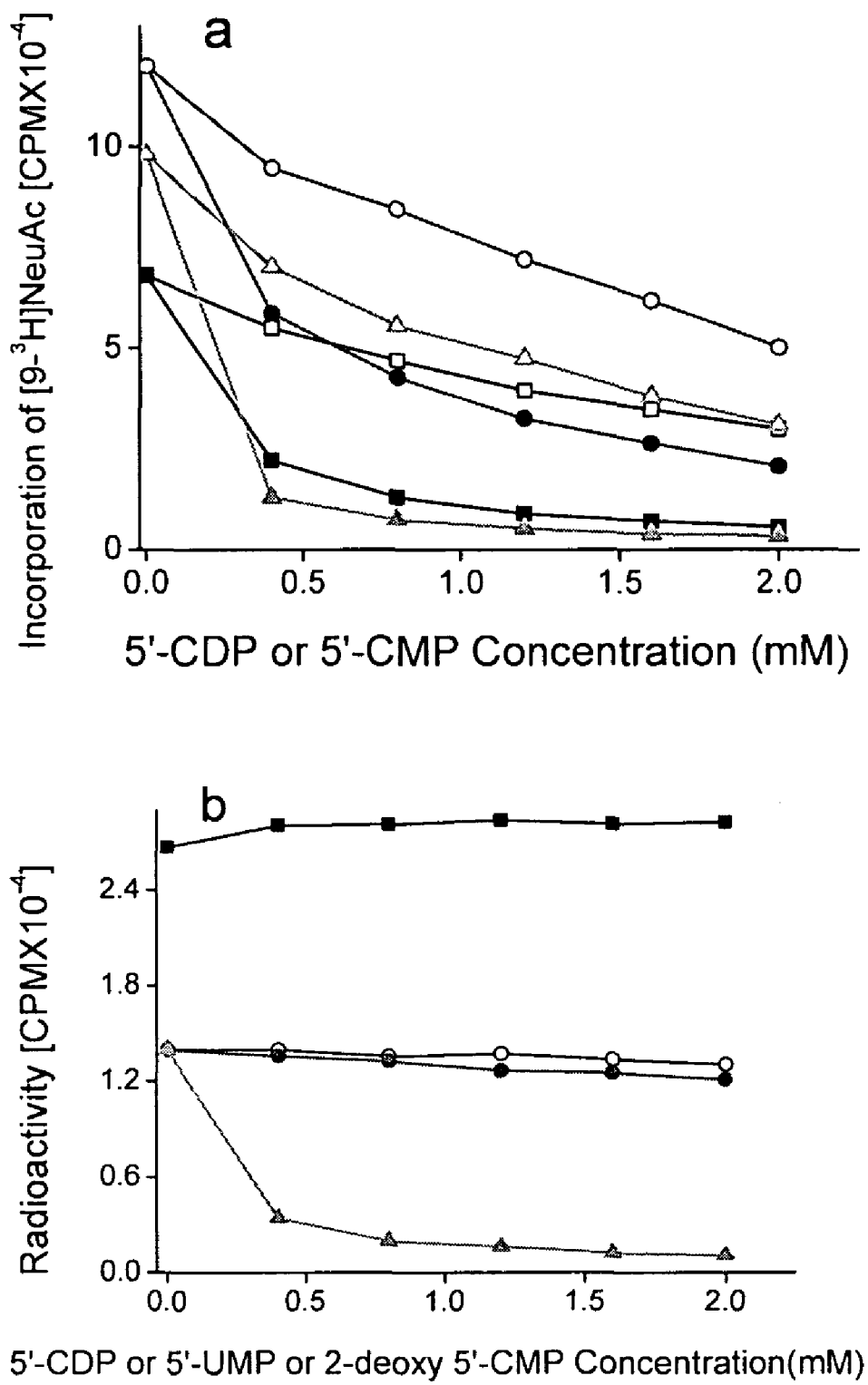
FIG. 5. Effect of 5'-nucleotides on direct sialyltransferase activity (panel a) and reverse sialylation (panel b). a. Varying concentrations of 5'-CDP or 5'-CMP were added to 100 mM acceptor (specified below), 0.15 mM CMP-[9-³H]NeuAc and either ST3Gal-II (0.2 mU), ST3Gal-III (0.5 mU) or ST6Gal-I (0.2 mU) for 4 h at 37° C. Products were separated using Sep-Pak C18 method. ST3Gal-III activity was measured using acceptor 4-O-MeGalβ1,4GlcNAcβ-O-Bn in the presence of 5'-CDP (●) and 5'-CMP (○). ST6Gal-I activity was measured using Gal β1,4GlcNAcβ-O-Bn in the presence of 5'-CDP (▲) and 5'-CMP (△). ST3Gal-II using D-Fucβ1,3GalNAcα-O-Bn [5] in the presence of 5'-CDP (■) and 5'-CMP (□). b) Reverse sialylation by ST3Gal-II was measured in reaction mixtures containing 0.2 mM [9-³H] [3], 7 mM 5'-CMP, ST3Gal-II (2 mU), D-Fucβ1,3GalNAcα-OBn (3.0 mM) and varying doses of either 5'-CDP (▲), 5'-UMP (○) or 2-deoxy 5'-CMP (●) for 4 hours at 37° C. Reaction product ([9-³H]NeuAcα2,3DFucβ1,3 GalNAcα-O-Bn) was isolated using Sep-Pak C18 method. In some runs, where [5] was absent, the amount of CMP-NeuAc produced was quantified using the Dowex-1 Formate method in the presence of varying doses of 5'-CDP (■).

The effect of 5'-nucleotides on forward sialylation (FIG. 5a) and reverse sialylation (FIG. 5b) were examined. As seen in FIG. 5a, both 5'-CDP and 5'-CMP inhibited the forward sialylation activities of ST3Gal-II, ST3Gal-III, and ST6Gal-I using the sialyl donor CMP-[9-$^3$H]NeuAc and specific acceptors for the respective enzymes. 5'-CDP was a more potent inhibitor in all cases. In studies of reverse sialylation (FIG. 5b), 5'-CDP did not inhibit the first step in the reverse sialylation reaction of ST3Gal-II namely the formation of CMP-[9-$^3$H]NeuAc from 5'-CMP. The overall formation of [9-$^3$H] NeuAcα2,3D-Fucβ1,3 GalNAcα-O-Bn by the two-step reverse sialylation process, however, was inhibited by 5'-CDP and this is consistent with the finding that 5'-CDP inhibits forward sialylation in the second step. 5'-UMP and 2-decxy 5'-CMP served as controls in these experiments since they did not alter the extent of product formation (FIG. 5b). Overall, our studies show that 5'-CDP inhibits the forward sialylation reaction without altering the reverse reaction.

Figure 6:
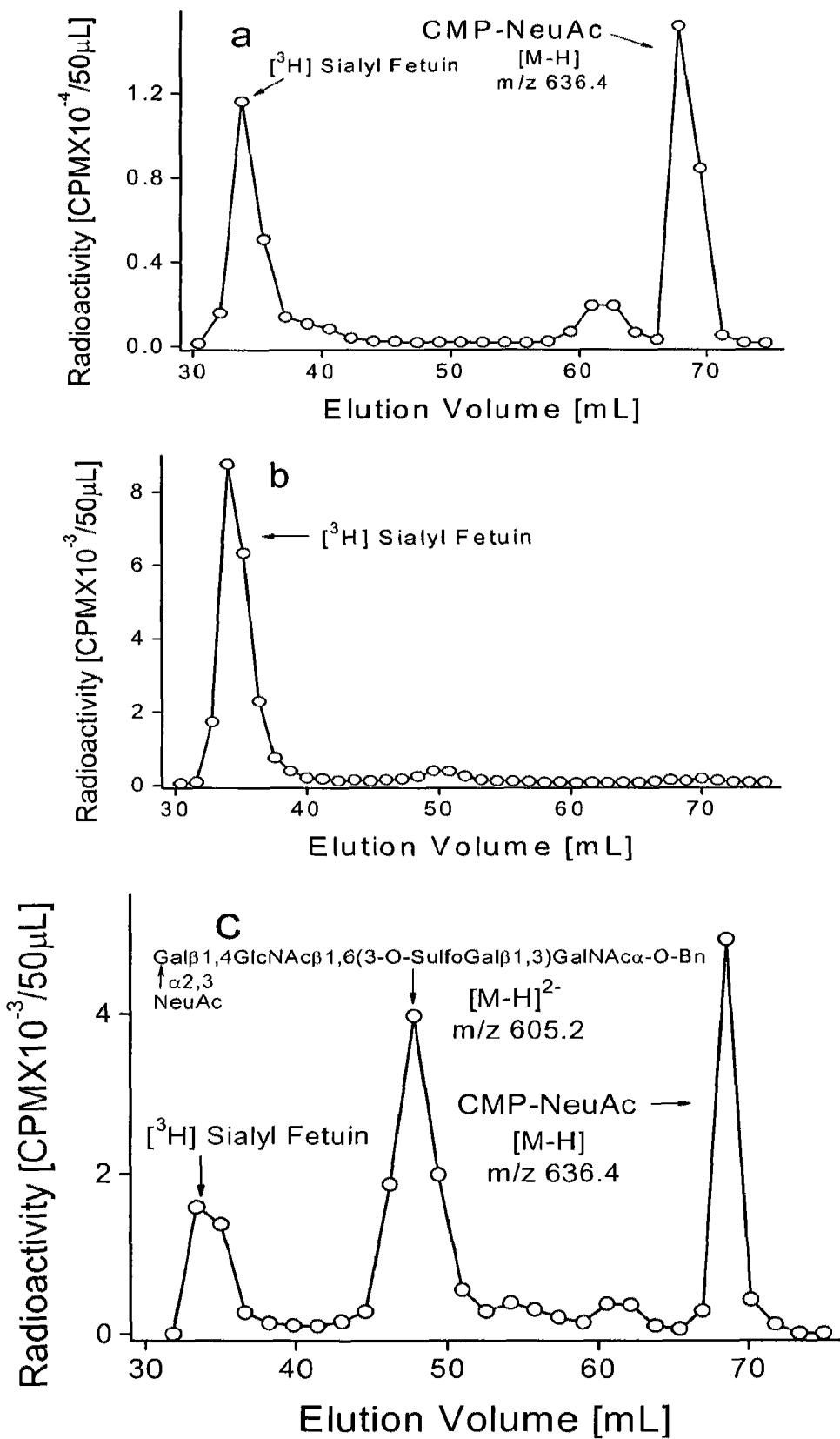
FIG. 6. Effect of sialyl or sulfo substituents in O-glycan chain on the reverse sialylation by ST3Gal-II. Incubation mixtures (600 μl) contained [9-³H] sialyl fetuin (5 mg), 200 mM NaCa Codylate pH 6.0, 20 mM 5'-CMP, 50 mM ST3Gal-II and the following: a. 6.0 mM NeuAcα2,3Galβ1, 4GlcNAcβ1,6 (Galβ1,3)GalNAcα-O-Bn, b. 6.0 mM 3-O-SulfoGalβ1,4GlcNAcβ1,6(Galβ1,3)GalNAcα-O-Bn or c. 6.0 mM Galβ1,6GlcNAcβ1,6(3-O-Sulphoβ1,3Gal)Gal-NAcα-O-Bn along with 50 mU ST3Gal-III. Products were fractionated using Biogel P₂ column after 20 h at 37° C. Unused [9-³H] sialyl fetuin (peak 1) appears prior to [9-³H] Sialyl product from acceptor (peak 2) and CMP-[9-³H] NeuAc (peak 3). Product identities were verified using LC-MS as indicated by molecular weights noted in the panels.

Effect of O-Glycans with Sialyl or Sulfo Substituents on Reverse Sialyltransferase Activity Another distinction between forward and reverse sialylation was observed in studies where the effect of three compounds, NeuAcα2,3Galβ1,4 GlcNAcβ1,6(Galβ1,3)GalNAcα-O-Bn (FIG. 6a), 3-O-SulfoGalβ1,4GlcNAcβ1,6(Galβ1,3)GalNAcα-O-Bn (FIG. 6b) and Galβ1,4GlcNAcβ1,6(3-O-SulfoGalβ1,3)GalNAcα-O-Bn (FIG. 6c), on the sialylation reaction was measured. For these studies, [9-$^3$H]sialyl fetuin was prepared by the action of ST3Gal-II on fetuin in the presence of CMP-[9-$^3$H]NeuAc. Radioactivity incorporation into the O-glycan chain of the glycoprotein was confirmed by treating the labeled molecule with alkaline borohyrdride (1MNaBH$_4$ in 0.1MNaOH at 45° C. for 24 hours) and detecting the released radioactivity. During these studies, sialyl fetuin was incubated with 5'-CMP, one of the above mentioned compounds, and sialyltransferase for 20 hours, and the product formed was eluted using a Biogel P$_2$ column. As seen in FIG. 6, the radioactivity associated with fetuin can be resolved from that associated with CMP-NeuAc and the synthetic acceptor. Here, it is observe that 3-O-SulfoGalβ1,4GlcNAcβ1,6(Galβ1,3)GalNAcα-O-Bn (FIG. 6b) inhibits formation of the intermediate CMP-NeuAc. Consequently no radioactivity was associated with the acceptor. NeuAcα2,3Galβ1,4GlcNAcβ1,6(Galβ1,3)GalNAcα-O-Bn (FIG. 6a), on the other hand, prevents product formation without inhibiting CMP-NeuAc formation. Finally, Galβ1,4GlcNAcβ1,6(3-O-SulfoGalβ1,3)GalNAcα-O-Bn permits both the formation of CMP-NeuAc from 5'-CMP, and the transfer of [9-$^3$H]NeuAc from the newly synthesized CMP-[9-$^3$H]NeuAc into Galβ1,4 GlcNAcβ1,6(3-O-SulfoGalβ1,3)GalNAcα-O-Bn in the presence of ST3Gal-III (FIG. 6c). The use of distinct compounds to differentially alter reverse and forward sialylation function further supports the concept that ST3Gal-II may have more than one catalytic function.

Figure 7:
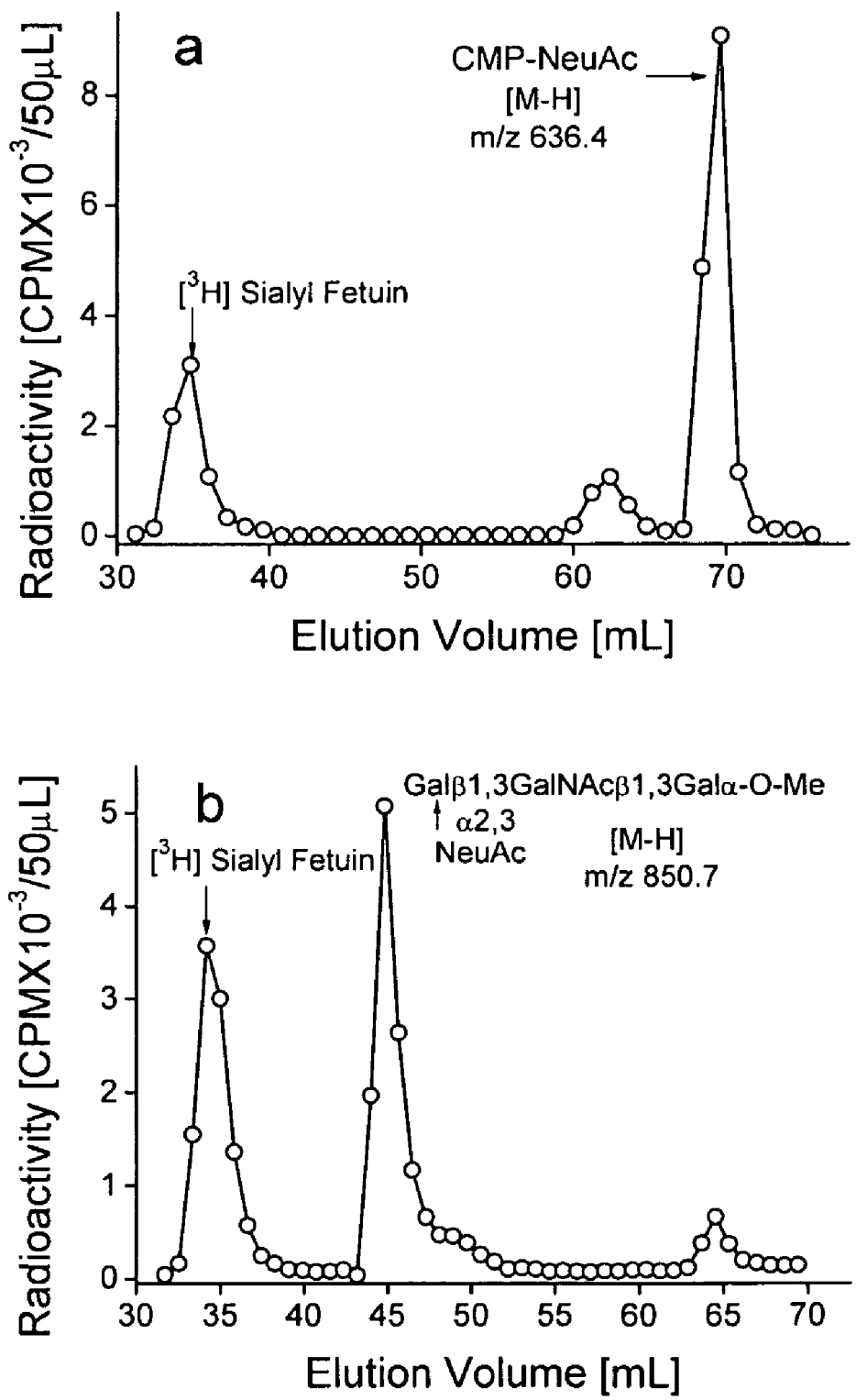
FIG. 7. Sialylation of Globo backbone structures by reverse sialylation of ST3Gal-II. Incubation mixtures (500 μl) contained [9-³H] sialyl fetuin (5 mg), 200 mM NaCa Codylate pH 6.0, 20 mM 5'-CMP and the following: a. 50 mU ST3Gal-II and b. 6.0 mM Galβ1,3GalNAcβ1,3Gala-O-Me and 50 mU ST3Gal-II. Reaction products were isolated using Biogel P₂ column after 20 hours at 37° C. and product identity was verified by mass spectrometry as indicated by the molecular weights in the panel. Peak I: Unused [9-³H] sialyl fetuin; Peak II: [9-³H] sialyl product from acceptor; Peak III: CMP-[9-³H]NeuAc from 5'-CMP.

Reverse Sialylation Activity of ST3Gal-II Allows Formation of Sialylated Globo Backbone Structure from Sialyl Fetuin As shown in FIG. 7a, [9-$^3$H]sialyl fetuin served as a donor that allowed the formation of CMP-[9-$^3$H]NeuAc by ST3Gal-II through the reverse sialylation mechanism. FIG. 7b further shows that ST3Gal-II can synthesize NeuAcα2,3Galβ1,3GalNAcβ1,3Galα-O-Me from [9-$^3$H] sialyl fetuin using reaction scheme-II. Thus, sialyl fetuin may be a useful compound for the inexpensive, enzymatic synthesis of an array of α2,3sialylated compounds including globo backbone based analogs.

Figure 8:
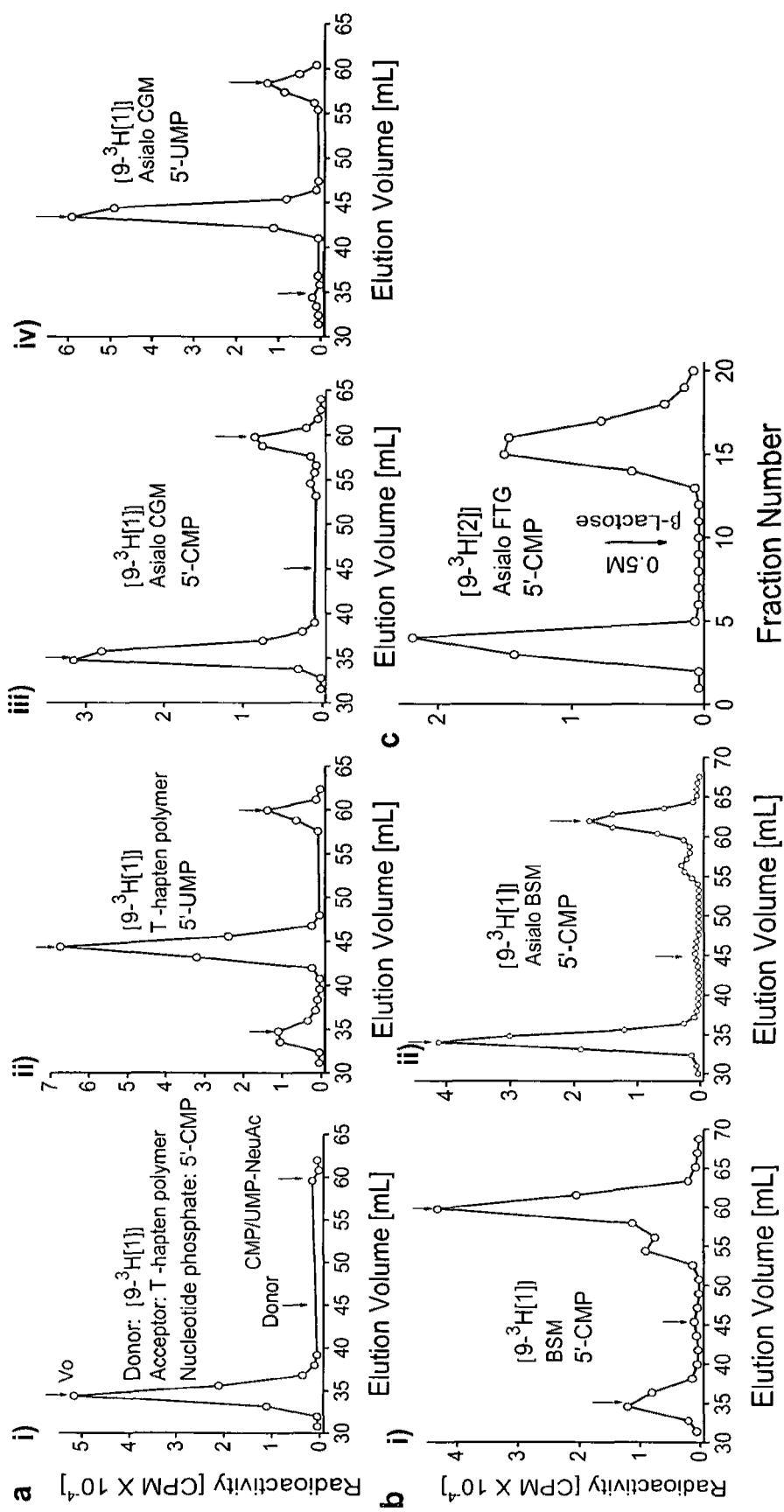
FIG. 8. Catalytic activity of ST3Gal-II towards macromolecules following reaction scheme-II. a. Transfer of [9-³H] NeuAc from 0.15 mM [[9-³H][1]] to 2 mg Galβ1,3GalNAcα-O—Al/AA-CP using 3 mU ST3Gal-II in the presence of: i) 0.7 mM 5'-CMP, ii) 0.7 mM 5'-UMP, and to 2 mg asialo CGM (porcine Cowper's Gland Mucin) in the presence of iii) 0.7 mM 5'-CMP and iv) 0.7 mM 5'-UMP. b. Transfer of [9-³H] NeuAc to 2 mg bovine submaxillary mucin (BSM, panel i) and its asialo derivative (2 mg asialo BSM, panel ii) from donor 0.15 mM [[9-³H] [1]] by the cloned 3 mU ST3Gal-II using 0.7 mM 5'-CMP. Reactions took place for 18 h. at 37° C. under conditions described in FIG. 1, and products were isolated using Biogel P2 chromatography for all data in a. and b. In each case, the first peak that appears with the void volume (V₀=35 mL) corresponds to the sialylated macromolecule, the second peak is the unused donor and the third CMP- or UMP-[9-³H]NeuAc formed in the reaction. In all panels, donors are depicted in red, acceptor in green and nucleotide phosphate in blue. c. Transfer of [9-³H]NeuAc to 0.6 mg Fetuin Triantennary asialo glycopeptide (asialo FTG) from donor [[9-³H] [2]] by the cloned 0.75 mU ST6Gal-I and 0.75 mU ST3Gal-II using 1.2 mM 5'-CMP. Reaction was carried out for 19 h at 37° C. Following this, the reaction mixture was diluted with 1.0 ml of 10 mM Hepes pH7.5 containing CaCl₂ and MnCl₂ and subjected to SNA-agarose affinity chromatography to bind α2,6 linked NeuAc. Bound product was released by 0.5M β-lactose at fraction 10 and radioactivity was measured. 57% of [9-³H]NeuAc was bound to column indicating the formation of α2,6 sialylated macromolecule.
Figure 9:
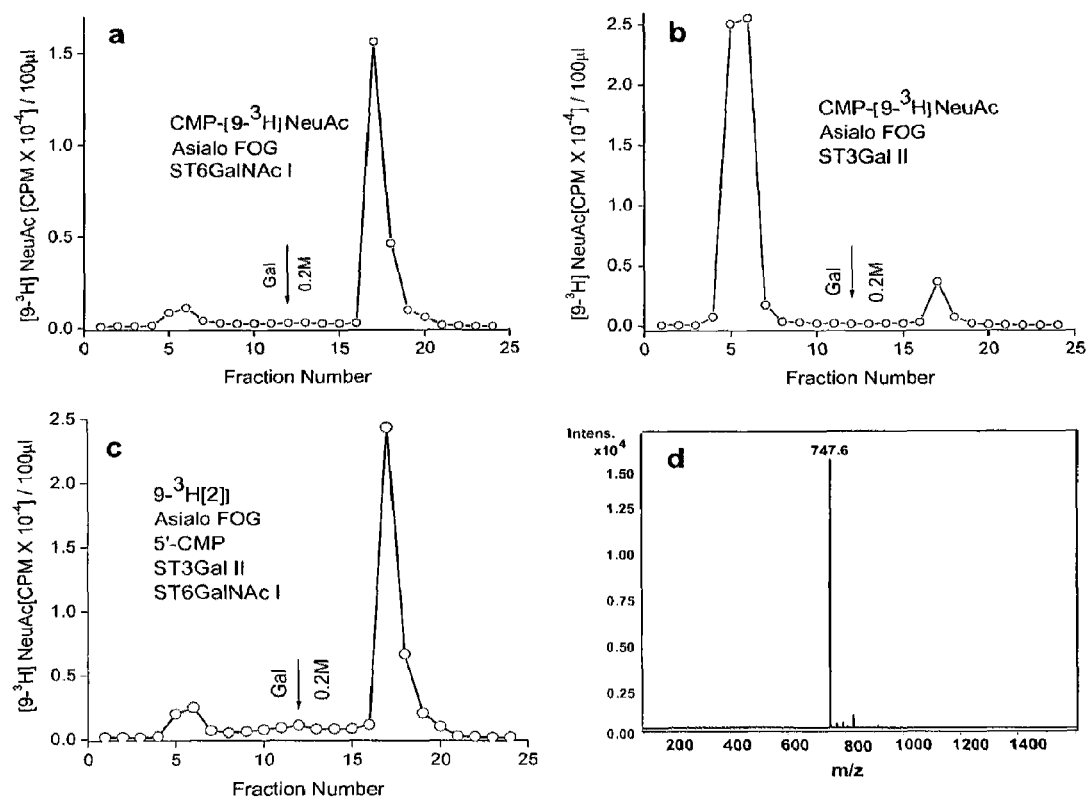
FIG. 9. Scheme-II using acceptor Fetuin O-glycosidic asialo GP (asialo FOG). a. When 0.4 mg asialo FOG was [9-³H]sialylated with 2.0 mM CMP-[9-³H]NeuAc and 10 mU ST6Gal-I (Chicken) at 37° C. for 20 h, more than 90% of the radioactivity bound PNA-agarose suggesting that the product was α2,6 sialylated. b. Incubation with Gal3ST-II, instead of ST6Gal-I, however, resulted in product that did not bind PNA agarose. c. When 2.0 mg asialo FOG was incubated with 2.0 mM CMP, donor 0.15 mM [9-³H]NeuAcα2,3Galβ1, 3(4-F GlcNAcβ1,6)GalNAcα-O-Bn and two sialyltransferases (4.0 mU ST3Gal-II and 10.0 mU ST6GalNAc I) for at 37° C. 20 h. (panel c), more than 90% of the product bound PNA-agarose. The results indicate that 5'-CMP was converted to CMP-NeuAc by ST3Gal-II and this intermediate was utilized by ST6GalNAc I to synthesize [9-³H]NeuAcα2, 6(Galβ1,3)GalNAcα-O-Ser/Thr units. d. Transfer of sialic acid from Fetuin O-glycosidic sialo GP (FOG) to D-Fucβ1, 3GalNAcα-O-Bn was assessed using mass spectroscopy. First α2,3[9-³H]FOG was synthesized by incubating 0.4 mg asialo-FOG with 1.0 mM CMP-[9-³H]NeuAc and 1.5 mU cloned ST3Gal-II, and separating product using Biogel P2 column. 6µ mol D-Fucβ1,3GalNAcα-O-Bn, 20µ mol CMP, 4 mg (3 µmol) FOG containing the above isolated α2,3[9-$^3$H] FOG and 80 mU/mL ST3Gal-II were then incubated at 37° C. for 16 h. The reaction mixture was fractionated on Biogel P2 column to separate the radioactive product arising from D-Fucβ1,3GalNAcα-O-Bn from the unused radioactive Fetuin GP. The product arising from D-Fucβ1,3GalNAcα-O-Bn was identified by Mass Spectral analysis as NeuAcα2,3D-Fucβ1,3GalNAcα-O-Bn (Theoretical M. W. 748.7). The yield of this product was 0.63 µmol since 20% of radioactivity from FOG was transferred.

CMP-NeuAc Formed by Reverse Sialylation Serves as a Sialyl Donor for Macromolecules in the Presence of ST3Gal-II, ST6Gal-I and ST6GalNAc-I The ability of scheme-II to mediate the formation of sialylated macromolecules was studied using CGM (porcine Cowper's Gland Mucin, FIG. 8a), BSM (Bovine Submaxillary Mucin, FIG. 8b), Anti-Freeze glycoprotein FTG (Fetuin Triantennary glycopeptide, FIG. 8c) and FOG (Fetuin O-glycosidic glycopeptides, FIG. 9). In the case of CGM (FIG. 8a), the acrylamide copolymer Galβ1,3GalNAcα-O—Al/AA-CP (a synthetic macromolecular acceptor) and asialo CGM were incubated separately with donor [9-$^3$H[1]] and ST3Gal-II in the presence of either 5'-CMP or 5'-UMP for 21 hours at 37° C., and then subjected to Biogel P2 chromatography to separate [9-$^3$H]sialyl macromolecule from [9-$^3$H]sialyl donor and CMP- or UMP-[9-$^3$H]NeuAc. Both the acrylamide copolymer and asialo CGM served as good acceptors in the presence of 5'-CMP whereas lower amounts of sialylated macromolecules were formed in the presence of 5'-UMP (FIG. 8a). UMP-sialic acid was a poor donor of sialic acid for not only ST3Gal-II but also ST3Gal-III and ST6Gal-I (Table VI).

Figure 13:
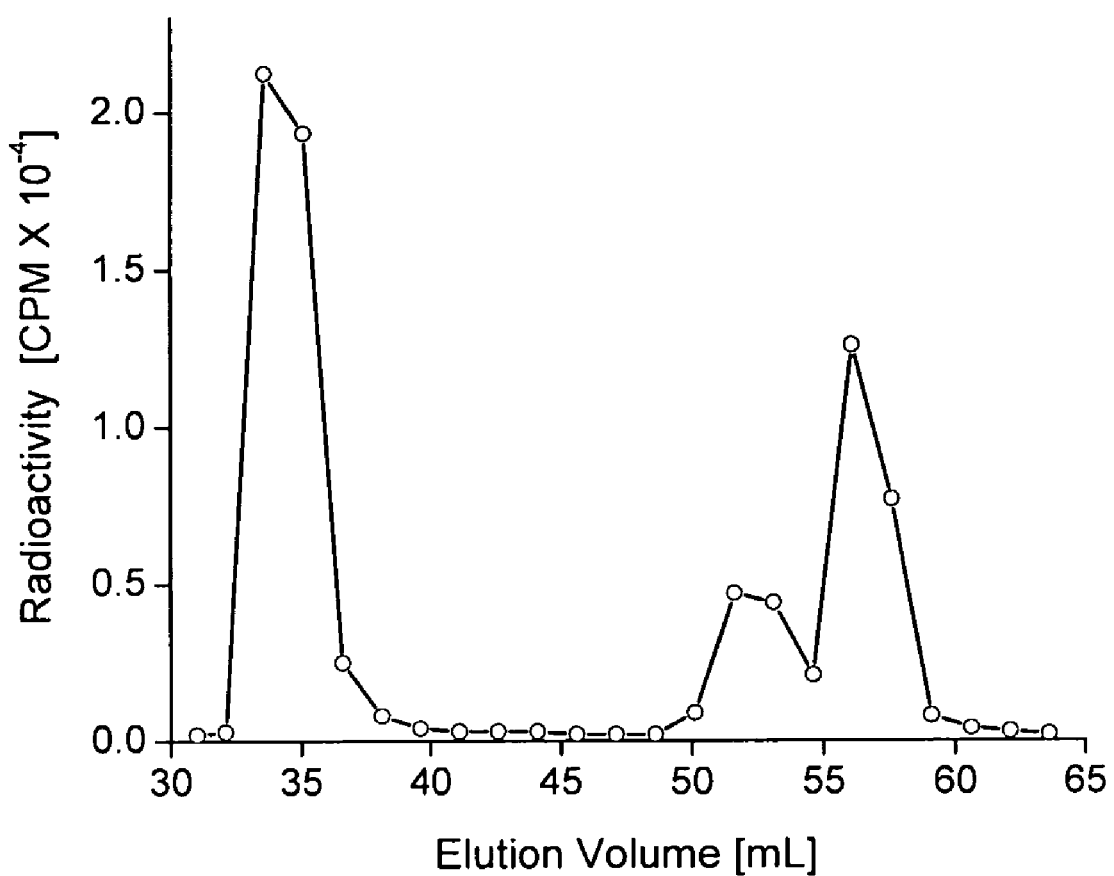
FIG. 13. Transfer of [9-$^3$H]NeuAc to 5'-CMP from the donor [9-$^3$H] sialylated CGM. [9-$^3$H] sialylated CGM was first isolated by incubating asialo CGM with CMP-[9-$^3$H] NeuAc and clonal ST3Gal-II for 20 h at 37° C. and then purification of macromolecule using Biogel P2 chromatography. This isolated [9-$^3$H] sialyl CGM (1 mg) was subsequently incubated with 1.0 mM 5'-CMP and 1.5 mU clonal ST3Gal-II for 20 h at 37° C. and then the reaction mixture was subjected to Biogel P2 chromatography. About 43% of [9-$^3$H] NeuAc was identified with the peak of CMP-NeuAc. Thus, the clonal ST3Gal-II was capable of synthesizing CMP-NeuAc from 5'-CMP by utilizing a 2,3 sialyl T-hapten units of CGM.

[9-$^3$H] Sialylated CGM could also act as donor to form CMP-[9-$^3$H]NeuAc in presence of 5'-CMP and ST3Gal-II (FIG. 13). [9-$^3$H] sialylated CGM was first synthesized using CGM and CMP-[9-$^3$H]NeuAc in the presence of ST3Gal-II. Subsequently, it was observed that the radiolabeled CGM could donate [9-$^3$H]NeuAc to 5'-CMP in the presence of ST3Gal-II to form new CMP-[9-$^3$H]NeuAc.

Similar to the case of CGM (FIG. 8a), BSM and asialo BSM also resulted in the efficient formation of radiolabeled sialylated macromolecules using ST3Gal-II, [9-$^3$H[1]] and 5'-CMP (FIG. 8b), with 58.5% and 19.7% of the [9-$^3$H]sialyl products being associated with asialo BSM and BSM respectively. There was no remaining unused donor. Some unused intermediate CMP-[9-$^3$H]NeuAc remained.

α2,6[9-$^3$H] sialylated FTG could be formed using 5'-CMP and asialo FTG upon incubation with donor [9-$^3$H[2]] and two enzymes ST3Gal-II and ST6Gal-I simultaneously (FIG. 8c). Here, reverse sialylation using ST3Gal-II and 5'-CMP resulted in the formation of CMP-NeuAc. The newly formed CMP-NeuAc was then acted upon by ST6Gal-I to form α2,6 sialylated FTG.

Similar results were observed with FOG using PNA-agarose chromatography. In these studies, the formation of either [9-$^3$H]NeuAcα2,6(Galβ1,3)GalNAcα-O-Ser/Thr or [9-$^3$H]NeuAcα2,3Galβ1,3GalNAcα-O-Ser/Thr units was detected upon incubation of asialo FOG and CMP-[9-$^3$H] NeuAc with ST6GalNAc-I (FIG. 9a) or ST3Gal-II (FIG. 9b) respectively. Here, the α2,6-sialylated compound formed in FIG. 9a bound PNA-agarose. The incubation of asialo FOG with 5'-CMP, the donor [9-$^3$H[2]], ST3Gal-II and ST6GalNAc-I also gave rise to product that bound PNA agarose (FIG. 9c). This observation is consistent with the notion that CMP-NeuAc can be formed from 5'-CMP by reverse sialylation in the presence of ST3Gal-II. This new CMP-NeuAc can then be utilized by ST6GalNAc-I to form [9-$^3$H]NeuAcα2,6(Galβ1,3)GalNAcα-O-Ser/Thr units. Finally, it was observed that sialylated FOG itself could participate in reverse sialylation (FIG. 9d). Sialylated FOG for these runs was first enzymatically prepared by reacting asialo-FOG with CMP-[9-$^3$H]NeuAc in the presence of ST3Gal-II. Subsequently, it was observed that this sialylated-FOG could act as a sialic acid donor for D-Fucβ1,3GalNAcα-O-Bn in the presence of 5'-CMP and ST3Gal-II. The formation of NeuAcα2,3D-Fucβ1,3GalNAcα-O-Bn in the above experiment was verified using mass spectrometry.

Reversible Sialyltransferase Activity in Human Cells

While the above experiments were performed with cloned rat enzymes, we examined if human cells also exhibited this novel enzyme activity (Table VII). Thus, [9-$^3$H[4]] was used as donor and D-Fucβ1,3GalNAcα-O-Bn [5] as acceptor in the presence of 5'-CMP and solubilized cell extracts. Of the cells tested, human prostate cancer cell lines LNCaP and PC-3 contained significant reversible sialyltransferase activity. These results shows that reverse sialylation occurs in human cells also.

Tables

TABLE I

Reverse sialylation equilibrium constant

| Donor | Acceptor | $K_{eq}$ (dimensionless units) |
|---|---|---|
| [9-$^3$H]NeuAcα2,3Galβ1,3(4-FGlcNAcβ1,6)GalNAcα-O-Bn, [[9-$^3$H]2] | 5'-CMP | 0.35 |
| [9-$^3$H]NeuAcα2,3Galβ1,3GalNAcβ1,3Galα-O-Me, [[9-$^3$H]3] | 5'-CMP | 98.9 |
| [9-$^3$H]NeuAcα2,3Gal(1,3(Gal(1,4 GlcNAc(1,6)GalNAc(-O-Bn | 5'-CMP | 0.18 |

TABLE II*

Nucleotide phosphates participating in reverse sialylation

| Nucleotide Phosphate (1 mM) | Incorporation of [9-$^3$H]NeuAc** (44197 CPM) |
|---|---|
| 5'-CMP | 100.0 |
| NeuAc plus 5'-CMP | 100.3 |
| 3'-CMP | 2.4 |
| 5'-CDP | 28.4 |
| 5'-CMP plus 5'-CDP | 91.1 |
| 5'-CTP | 1.6 |
| NeuAc plus 5'-CTP | 0.8 |
| 2' deoxy 5'-CMP | 26.3 |
| 5'-UMP | 55.9 |
| 5'-GMP | 2.3 |
| 5'-AMP | 3.0 |
| 5'-TMP | 1.1 |
| 5'-IMP | 1.6 |

*Studies similar to FIG. 1 were performed. Different nucleotide phosphates were used at 1 mM each. Since only the donor and not the [9-$^3$H] sialyl product binds WGA-agarose, the fraction of radioactivity that did not bind the column was quantified to be the % [9-$^3$H] NeuAc incorporated into the nucleotide phosphate acceptor.
**Incorporation of [9-$^3$H]NeuAc expressed as percent of the CPM incorporated into 5'-CMP

TABLE III*

Incorporation of [9-$^3$H]NeuAc from donors**

| Acceptor (2.5 mM) | | [9-H]NeuAcα2,3Galβ1,3 (GlcNAcβ1,6)GalNAc α-O-Al [[9-$^3$H][1]] | [9-$^3$H]NeuAcα2,3Galβ1,3 (6-O-sulfoGlcNAcβ1,6) GalNAc-O-Al [[9-$^3$H][4] | [9-$^3$H]NeuAcα2,3Galβ1,3 GalNAcβ1,3Galα-O-Me [[9-$^3$H][3]] |
|---|---|---|---|---|
| D-Fucβ1,3GalNAcα-O-Bn | [5] | 100.0 (34569 CPM) | 100.0 (97675 CPM) | 100.0 (6224 CPM)*** |
| D-Fucβ1,3(GlcNAcβ1,6)GalNAcα-O-Bn | [6] | ND | 96.9 | 106.5 |
| 4-FGalβ1,3GalNAcα-O-Bn | [7] | 60.8 | 33.3 | 4.1 |
| Galβ1,3(6-O-Me)GalNAcα-O-Bn | [8] | 43.0 | 21.5 | 3.3 |
| 3-O-MeGalβ1,4GlcNAcβ1,6(Galβ1,3) GalNAcα-O-Bn | [9] | 22.4 | 10.0 | ND |
| Galβ1,4GlcNAcβ1,6(Galβ1,3) GalNAcα-O-Bn | [10] | 20.5 | 8.4 | ND |
| 4-O-MeGalβ1,3GalNAcα-O-Bn | [11] | 8.9 | 2.7 | 0.2 |
| Galβ1,4GlcNAcβ-O-Bn | [12] | ND | 1.9 | 0.5 |
| Galβ1,4GlcNAcβ1,6(4-O-MeGalβ1,3) GalNAcα-O-Bn | [13] | 1.3 | 0 | ND |

ND: Not Determined

*150 μM [9-$^3$H] labeled donor was incubated with 1 mM 5'-CMP and 2.5 mM either T-hapten or mucin core-2 based acceptor in the presence of 0.2 mU ST3Gal-5II for 4 hours. under reaction conditions identical to FIG. 1. Acceptors were separated from donor using C-18 cartridge due to hydrophobicity of Bn (Benzyl) group. Radioactivity of eluate was quantified. The blank containing no acceptor had CPM<100.
**Incorporation of [9-$^3$H] NeuAc expressed as percent of the CPM incorporated into [5]
***CPM for this donor is low since 10 fold cold CMP-NeuAc (i.e., lower specific radioactivity of CMP-[9-$^3$H]NeuAc) was used to synthesize it as compared to other two donors.

TABLE IV

Donor specificity for reverse sialylation

| Sialyl donor | 5'-CMP | Acceptor | Enzyme | Radiolabeled acceptor/product formed (CPM)** |
|---|---|---|---|---|
| [9-$^3$H] NeuAcα2,6Galβ1,4GlcNAc β-O-Al (0.05 mM, 48240 CPM) [14] | 0.8 mM | 2.5 mM Galβ1,4GlcNAcβ-O-Bn | 3 mU ST6Gal-I | 129 |
| [9-$^3$H] NeuAcα2,6Galβ1,4GlcNAc β-O-Al (0.05 mM, 48240 CPM) [14] | 0.8 mM | 2.5 mM Galβ1,4GlcNAcβ1,6(Galβ1,3) GalNAcα-O-Bn | 3 mU ST6Gal-I | 36 |
| [9-$^3$H] NeuAcα2,6Galβ1,4GlcNAc β-O-Al (0.05 mM, 48240 CPM) [14] | 0.8 mM | 2.5 mM Galβ1,4GlcNAcβ1,3Galβ1,4 GlcNAcβ-O-Bn Galβ1,4GlcNAcβ-O-Bn | 3 mU ST6Gal-I | 45 |
| [9-$^3$H] NeuAcα2,3Galβ1,4GlcNAc β-O-Al (0.05 mM, 64800 CPM) [15] | 0.8 mM | 2.5 mM Galβ1,4GlcNAcβ-O-Bn | 3 mU ST3Gal-III | 5 |
| [9-$^3$H] NeuAcα2,3Galβ1,4GlcNAc β-O-Al (0.05 mM, 64800 CPM) [15] | 0.8 mM | 2.5 mM Galβ1,4GlcNAcβ1,6(Galβ1,3) GalNAcα-O-Bn | 3 mU ST3Gal-III | 27 |

TABLE IV-continued

Donor specificity for reverse sialylation

| Sialyl donor | 5'-CMP | Acceptor | Enzyme | Radiolabeled acceptor/product formed (CPM)** |
|---|---|---|---|---|
| [9-$^3$H] NeuAcα2,3Galβ1,4GlcNAc β-O-Al (0.05 mM, 64800 CPM) [15] | 0.8 mM | 2.5 mM Gal(1,4GlcNAc(1,3Gal(1,4 GlcNAc(-O-Bn Gal(1,4GlcNAc(-O-Bn | 3 mU ST3Gal-III | 24 |
| [9-$^3$H] NeuAc(2,6Gal(1,4GlcNAc (-O-Al (0.05 mM, 48240 CPM) | 1.6 mM | 5 mM D-Fuc(1,3GalNAc(-O-Bn | 3 mU ST3Gal-II | <0* |
| [9-$^3$H] NeuAc(2,3Gal(1,4GlcNAc (-O-Al (0.05 mM, 64800 CPM) | 1.6 mM | 5 mM D-Fuc(1,3GalNAc(-O-Bn | 3 mU ST3Gal-II | <0* |

*zero indicates that value is slightly below background control levels

**Measured using C18 cartridge method. In all cases, reverse sialylation did not proceed to appreciable levels.

TABLE V

Effect of citrate ion on sialyltransferase activity*

| | Activity (Incorporation of [9-$^3$H]NeuAc) | | |
|---|---|---|---|
| | Without citrate CPM | With citrate (40 mM) CPM | Inhibition % |
| Forward Sialylation: Sialyltransferase [Acceptor] | | | |
| ST3Gal I (Cloned Human)$^a$ [Galβ1,3GalNAcβ-O-Al] | 24091 | 402 | 98.3 |
| ST3Gal II (Cloned rat liver)$^a$ [Galβ1,3GalNAcβ-O-Al] | 63760 | 33025 | 48.2 |
| ST3Gal III (Cloned rat liver)$^b$ [4-O-MeGalβ1,4GlcNAcβ-O-Bn] | 109634 | 39115 | 64.3 |
| ST6Gal I (Cloned rat liver)$^b$ [Galβ1,4GlcNAcβ-O-Bn] | 98633 | 7471 | 92.4 |
| Reversible Sialylation: [9-$^3$H] [3] is sialyl donor and ST3Gal-II is enzyme in all reaction mixtures: | | | |
| a) Synthesis of CMP-[9-$^3$H]NeuAc from 5'-CMP$^a$ | 42561 | 48800 | 0 |
| b) Synthesis of [9-$^3$H]NeuAcα2,3 D-Fucβ1,3GalNAcα-OBn Through 5'-CMP in above step$^b$ | 57986 | 59131 | 0 |

*For direct sialylation, incubation mixtures containing 1.0 mM acceptor, 0.15 mM CMP-[9-$^3$H] NeuAc, ST3Gal-I (0.2 mU) or ST3Gal-II (0.4 mU) or ST3Gal-III (0.5 mU) or ST6Gal-I (0.4 mU) were incubated at 37° C. for 4 hours in the presence or absence of 40 mM sodium citrate.
For reverse sialylation, incubation mixtures containing 0.16 mM [9-$^3$H][3], 20 mM 5'-CMP and ST3Gal-II (5.0mU) with and without 3.0 mM D-Fucβ1,3GalNAcα-OBn were incubated at 37° C. for 4 hours in the presence or absence of 40 mM Sodium Citrate.
$^a$processed by Dowex-l-Formate method; this enzyme was kindly provided by Dr. J. T. Y. Lau (RPCI).
$^b$processed by Sep-Pak C18 method

TABLE VI

CMP-NeuAc but not UMP-NeuAc formed by reverse sialylation is an efficient sialyl donor for forward sialyltransferase reaction

| | | Reverse sialylation | |
|---|---|---|---|
| | | 5'CMP → CMP- [9-$^3$H]NeuAc | 5'UMP → UMP- [9-$^3$H] NeuAc |
| | | Incorporation of [9-$^3$H]NeuAc into the acceptor | |
| | | CPM | CPM |
| a) | ST3Gal-II activity [Acceptor: D-Fucβ1,3GalNAcα-O-Bn] | 134122 | 1243 |
| b) | ST3Gal-III activity [Acceptor: 4-O-MeGalβ1,4GlcNAcβ-O-Bn] | 59531 | 3804 |
| c) | ST6Gal-I activity [Acceptor: Galβ1,4GlcNAcβ-O-Bn] | 15066 | 182 |

*Incubation mixtures run in duplicate contained the sialyl donor [[9-$^3$H][3]] (0.0625 mM), 8 mM 5'-CMP (first column) or 5'-UMP (second column) and benzyl disaccharide glycoside acceptor (2.5 mM). In addition: a) contained 3.0 mU of ST3Gal-II, b) contained 3.0 mU each of ST3Gal-II and ST3Gal-III, and c) contained 3.0 mU of ST3Gal-II and 1.0 mU of ST6GalI. Blank samples did not contain 5'-CMP or 5'UMP.
The reaction mixtures described above were incubated for 4 h at 37° C. and then processed using Sep-Pak C18 method, which binds benzyl glycosides. The amount of [9-$^3$H] NeuAc transferred from donor to individual acceptors was obtained after subtracting blank values (<400 CPM). The variation of duplicate values was less than 5% in all cases.

TABLE VII

Reversible sialyltransferase activity in human cancer cell lines

| Cancer Cell Lines | Transfer of [9-$^3$H]NeuAc from [9-$^3$H][4] to [5] CPM × $10^{-3}$/mg protein |
|---|---|
| BREAST: | |
| T47D | 0.52 |
| ZR75-1 | 1.32 |
| MDA-MB231 | 0.09 |
| MDA-MB-435 | 0.69 |
| MCF-7 | 0.57 |
| COLON: | |
| LS180 | 0.01 |
| PROSTATE: | |
| LNCaP | 19.89 |
| PC3 | 4.72 |
| LEUKEMIA | |
| HL60 | 0.76 |

*0.15 mM [9-$^3$H]NeuAcα2,3Galβ1,3(6-O-sulfo GlcNAcβ1,6)GalNAc-O-Al[9-$^3$H][4]] was added to 3.0 mM D-Fucβ1,3GalNAcα-O-Bn [5] in the presence of 1.0 mM 5'-CMP and 100 μl Triton-X solubilized cell extract for 16 h. at 37° C. at pH 6.0. Total reaction volume was 180 μl. The product [9-$^3$H]NeuAcα2,3D-Fucβ1,3GalNAcα-O-Bn was measured using Sep-Pak C18 separation followed by liquid scintillation counting.

Example 2

This example describes mammalian sialyltransferase ST3Gal-II as an enzymatic exchanger of sialyl residues and as a precision tool for studying mucin-type sialylated structures in health and disease.

Experimental Techniques

Rat recombinant ST3Gal-II (α2,3(0)ST) was purchased from Calbiochem. Three different lots of ST3Gal-II purchased from Calbiochem and used in this study yielded similar results. CMP-NeuAc was obtained from Sigma. All enzymatic sialylation reactions were typically carried out in NaCa Codylate buffer pH6.0 in presence of enzyme acceptor CMP-[9-$^3$H]NeuAc or (NEN-DuPont) CMP[$^{14}$C]NeuAc. The concentration of total CMP-NeuAc was adjusted in individual reactions by supplementing with non-radioactive CMP-NeuAc. Products formed were separated using different chromatograph procedures.

a) Gel chromatography on Biogel P2 and P6 columns: A Biogel P2 column or Biogel P6 column (Fine Mesh; 1.0×116.0 cm) was used with 0.1 M pyridine acetate (pH5.4) as the eluent at room temperature. In cases where radiolabeled compounds were prepared using this column, the peak fraction containing radioactivity was collected, lyophilized to dryness, dissolved in small volume of water and stored frozen at −20° C. for further experimentation.

b) Lectin-agarose affinity chromatography: A column of 7 ml bed volume of WGA-, VVL- or Con A-agarose (Vector Lab, Burlingame, Calif.) was employed.

c) Thin layer chromatography: TLC was carried out on Silica gel GHLF (250 μm scored 20×20 cm; Analtech Newark Del.). The solvent systems 1-propanol/NH$_4$OH/H$_2$O (12/2/5 v/v), CHCl$_3$/CH$_3$OH/H$_2$O (5/4/1 v/v) and Ethyl acetate/pyridine/H$_2$O/Acetic acid (5/5/3/1 v/v) were used. The acceptor compounds were located on the plates by spraying with sulfuric acid in ethanol and heating at 100° C. The radioactive products were located by scraping 0.5 cm width segments of silica gel and soaking in 2.0 ml water in vials followed by liquid scintillation counting. $^{14}$C-sialyl compounds were also visualized by autoradiography of TLC plates.

d) Pronase digestion of labeled glycoproteins followed by separation on Biogel P6 column.

e) Mild alkaline borohydride treatment of labeled glycoproteins followed by separation on Biogel P6 column.

f) SDS-Page of $^{14}$C sialyl labeled glycoproteins.

Preparation of [$^{14}$C] sialyl fetuin: Fetuin (Sigma F.3004; 30 mg) was incubated with CMP[$^{14}$C]NeuAc (NEN DuPont) (1.5 μCi) and cloned ST3Gal-II (CalBiochem) (100 mU) in 0.8 ml of 0.2M NaCa Codylate pH6.0 for 20 h at 37° C. The reaction mixture was chromatographed on the Biogel P2 column. The first peak of radioactive material emerging at the void volume contained [$^{14}$C] labeled fetuin and this pool of fractions was lyophilized to dryness.

Radiolabeling of bovine brain gangliosides using CMP-[9-$^3$H]NeuAc or CMP-[$^{14}$C]NeuAc and cloned ST3Gal-II: Bovine brain gangliosides mixture (CalBiochem; 13 mg) was incubated with 20 μCi of CMP-[9-$^3$H]NeuAc (NEN) and 200 mU of ST3GalIII in 1.2 ml of 0.15M NaCa Codylate pH6.0 at 37° C. for 20 h. Then this reaction mixture was fractionated on the Biogel P2 column. The first peak of radioactivity emerging in this void volume was collected and lyophilized to dryness. This [$^3$H] labeled ganglioside mixture was further purified on the Biogel P6 column from which it emerged on a peak in the void volume. This fraction was lyophilized to dryness.

Bovine brain ganglioside mixture (Calbiochem; 25 mg) was incubated with CMP-[$^{14}$C]NeuAc (NEN) (4 μCi) and 200 mU of ST3Gal-II in 1.2 ml of 0.15M NaCa Codylate pH6.0 at 37° C. for 20 h. Then this reaction mixture was chromatographed on the Biogel P6 column for the isolation of [$^{14}$C] labeled gangliosides as described above.

Results

Exchange of Sialic Acid Between CMP-NeuAc and O-Glycan Donor.

CMP-[9-$^3$H]NeuAc in the presence of ST3Gal-II and the tetrasaccharide molecule NeuAcα2,3Galβ1,3(GlcNAcβ1,6)GalNAcα-O-Bn [1] resulted in the formation of a radiolabeled product that behaved identically to [1].

Enzymatic Exchange Resulting in the Distribution of Both [9-$^3$H] and [$^{14}$C] Sialyl Residues in Fetuin, NeuAcα2,3Galβ1,3GalNAcβ1,3Gala-O-Me and CMP-NeuAc:

[$^{14}$C] Sialyl fetuin (2 mg in 100 μl water) was mixed with 100 μl of [9-$^3$H]NeuAcα2,3Galβ1,3GalNAcβ1,3Gala-O-Me (0.75 mm) and incubated in a reaction volume of 400 μl containing 0.15M NaCa Codylate pH6.0, 10 mM 5'-CMP and 100 mU of cloned ST3Gal-II at 37° C. for 20 h. Another identical incubation mixture containing everything except 5'-CMP was also incubated at the same time. Both reaction mixtures were diluted to 1.0 ml with water and then fractionated separately on the Biogel P2 column. The results indicated that an exchange of [$^{14}$C] sialyl group from [$^{14}$C] sialyl fetuin and [9-$^3$H] sialyl group from [9-$^3$H]NeuAcα2,3Galβ1,3GalNAcβ1,3Gala-O-Me has taken place in presence of 5'-CMP, which was converted to the intermediate compounds CMP-[$^{14}$C]NeuAc and CMP-[9-$^3$H]NeuAc.

Identification of Specific Exchange of [$^{14}$C] or [9-$^3$H] Sialyl Residue with NeuAc Linked α2,3 to Galβ1,3GalNAc Unit Containing Gangliosides:

Both [9-$^3$H] and [$^{14}$C] sialic acid labeled bovine brain ganglioside mixtures were subjected to TLC using CHcl$_3$:CH$_3$OH:0.2% aqueous CaCl$_2$ (v/v 60:40:9) as the solvent system. The radioactivities were located on the TLC plates by scraping silica gel from 0.5 cm width segments of the TLC plates and then counting the radioactivity after soaking silica in 2.0 ml water by scintillation counting. The third TLC plate containing [$^{14}$C] sialyl ganglioside mixture was developed by autoradiography and the fourth containing [$^{14}$C] Sialyl gangliosides mixture was sprayed with H$_2$504 in ethanol and heated on a hot plate for charring in order to locate the migration of gangliosides. It was found that both [9-$^3$H] and [$^{14}$C] radioctivities could be located with GD$_1$a and GT$_1$b but not with GM$_1$. The results thus indicate that sialic acid linked α2,3 to β1,4 linked Gal as occurring in GM$_1$ is not exchanged by ST3Gal-II whereas NeuAc residue linked α2,3 to Galβ1,3GalNAc- as present in GD$_1$a and GT$_1$b are exchangeable Sialyl residues with CMP-sialic acid by the action of ST3Gal-II.

Example 3

This examples describes specific radiolabeling of sialyl residues in mucin-type structures by ST3Gal-II using reverse sialylation, due to its action as an enzymatic exchanger of sialyl residues, as illustrated below:

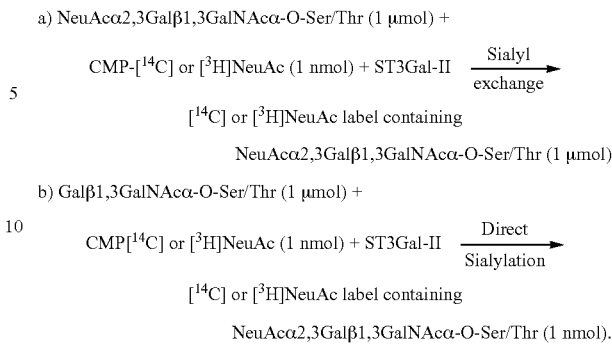

REFERENCES

1. Haverkamp, J., Spoormaker, T., Dorland, L., Vliegenthart, J. F. G. and Schauer, R (1979) Determination of the .beta.-anomeric configuration of cytidine 5'-monophospho-N-acetylneuraminic acid by carbon-13 NMR spectroscopy *J. Am. Chem. Soc.* 101, 4851-4853.
2. Kolter, T. and Sandhoff, K (1997) Sialic acids-why always α-linked *Glycobiology* 7, vii-ix.

The invention claimed is:

1. A method for sialylating an acceptor glycoconjugate comprising the steps of admixing in a vessel the following components to form a reaction mixture:
    a) a sialic acid donor other than a sialic acid-5'-nucleotide monophosphate (NMP);
    b) an acceptor glycoconjugate; and
    c) catalytic amount of exogenous mammalian ST3Gal-II sialyltransferase, under conditions such that a sialylated acceptor glycoconjugate is formed in the reaction mixture.

2. The method of claim 1, wherein the sialic acid donor is selected from the group consisting of glycoprotein and glycolipid.

3. The method of claim 2, wherein the glycoprotein is selected from the group consisting of mucin core-2 glycoprotein, mucin core-1 glycoprotein, fetuin, and Cowper's gland mucin (CGM).

4. The method of claim 2, wherein the glycolipid is a ganglioside.

5. The method of claim 1, wherein the acceptor glycoconjugate is selected from the group consisting of glycoprotein and glycolipid.

6. The method of claim 1, wherein the mammalian ST3Gal-II sialyltransferase is selected from the group consisting of recombinant rat ST3Gal-II and human ST3Gal-II.

7. The method of claim 1, wherein the conditions comprise a pH from 5.0 to 6.0.

8. The method of claim 1, wherein the conditions comprise a pH of 5.6.

9. The method of claim 1, wherein the sialic acid donor has a detectable label incorporated into the sialic acid moiety that is transferred to the acceptor glycoprotein.

10. The method of claim 9, wherein the detectable label is a radioactive isotope.

11. The method of claim 10, wherein the radioactive isotope is selected from the group consisting of tritium ($^3$H) and $^{14}$C.

12. The method of claim 1, wherein the reaction mixture further comprises 5'-cytidine monophosphate.

* * * * *